(12) United States Patent
Fostad Moe et al.

(10) Patent No.: US 12,127,747 B2
(45) Date of Patent: *Oct. 29, 2024

(54) TOURNIQUET

(71) Applicant: Aristeia AS, Oslo (NO)

(72) Inventors: Gard Fostad Moe, Oslo (NO); Gunnar-Magnus Larsen, Blystadlia (NO); Pål Halvorsen, Skedsmokorset (NO)

(73) Assignee: Aristeia AS, Oslo (NO)

( * ) Notice: Subject to any disclaimer, the term of this patent is extended or adjusted under 35 U.S.C. 154(b) by 390 days.

This patent is subject to a terminal disclaimer.

(21) Appl. No.: 17/589,858

(22) Filed: Jan. 31, 2022

(65) Prior Publication Data

US 2022/0151638 A1 May 19, 2022

Related U.S. Application Data

(63) Continuation-in-part of application No. 16/333,222, filed as application No. PCT/NO2017/050229 on Sep. 15, 2017, now Pat. No. 11,234,708.

(30) Foreign Application Priority Data

Sep. 15, 2016 (NO) .................................. 20161471

(51) Int. Cl.
*A61B 17/132* (2006.01)
*A61B 17/00* (2006.01)

(52) U.S. Cl.
CPC .............................. *A61B 17/1327* (2013.01); *A61B 2017/00407* (2013.01); *A61B 2017/00477* (2013.01)

(58) Field of Classification Search
CPC .............. A61B 17/132; A61B 17/1322; A61B 17/1327; A61B 2017/00407
See application file for complete search history.

(56) References Cited

U.S. PATENT DOCUMENTS 5,661,876 A * 9/1997 Goldenberg ............ F16L 33/02
24/19
7,582,102 B2 * 9/2009 Heinz ................ A61B 17/1327
606/203

(Continued)

FOREIGN PATENT DOCUMENTS

| EP | 2 672 937 A1 | 12/2013 |
| WO | WO 2012/109524 A1 | 8/2012 |
| WO | WO 2015/196255 A1 | 12/2015 |

OTHER PUBLICATIONS

International Search Report in International Application No. PCT/No. 2017/050229, dated May 2, 2018.

(Continued)

*Primary Examiner* — Ryan J. Severson
(74) *Attorney, Agent, or Firm* — Hershkovitz & Associates, PLLC; Abe Hershkovitz

(57) ABSTRACT

Apparatuses, components, devices, methods, and systems for tourniquets are provided. An example tourniquet includes a tensioning device having a housing and a pull-cord assembly and a strap that passes through the housing. An example strap has a first end and a second end. The example strap is arranged to together with the housing form a loop for encircling a limb. An example pull-cord assembly is configured to advance the strap through the housing to tighten the loop.

20 Claims, 17 Drawing Sheets

(56) References Cited

U.S. PATENT DOCUMENTS

| | | | |
|---|---|---|---|
| 8,043,327 B1* | 10/2011 | Arias | A61B 17/1322 600/499 |
| 8,065,781 B2* | 11/2011 | Chao | A61B 17/1327 254/365 |
| 8,635,746 B2* | 1/2014 | Bellamy | A61B 17/1327 24/193 |
| 8,652,164 B1 | 2/2014 | Aston | |
| 8,939,925 B2* | 1/2015 | Ingimundarson | A61F 5/028 602/19 |
| 9,750,507 B2* | 9/2017 | Brub | A61B 17/1327 |
| 9,844,385 B2* | 12/2017 | Dickinson | A61B 17/1322 |
| 9,924,949 B2* | 3/2018 | Benz | A61B 17/1325 |
| 10,258,347 B2* | 4/2019 | Hopman | A61B 17/1322 |
| 10,264,835 B2* | 4/2019 | Ingimundarson | A61F 5/028 |
| 10,363,046 B2* | 7/2019 | Hopman | A44B 11/266 |
| 10,695,071 B2* | 6/2020 | Ward | A61B 17/1322 |
| 11,234,708 B2* | 2/2022 | Fostad Moe | A61B 17/1327 |
| 11,291,461 B2* | 4/2022 | Hsiao | A61B 17/1325 |
| 11,504,136 B2* | 11/2022 | Rankins, III | A61B 17/1327 |
| 2005/0113866 A1 | 5/2005 | Heinz | |
| 2005/0267518 A1 | 12/2005 | Wright et al. | |
| 2006/0095072 A1 | 5/2006 | TenBrink et al. | |
| 2010/0137900 A1 | 6/2010 | Chao | |
| 2011/0247179 A1* | 10/2011 | Bellamy | A61B 17/1327 24/19 |
| 2012/0053617 A1* | 3/2012 | Benz | A61B 17/1325 606/203 |
| 2012/0150215 A1* | 6/2012 | Donald | A61B 17/1325 606/203 |
| 2012/0204381 A1 | 8/2012 | Ingimundarson et al. | |
| 2012/0215254 A1 | 8/2012 | Brub | |
| 2015/0051638 A1* | 2/2015 | Dickinson | A61B 17/1322 606/203 |
| 2015/0121657 A1 | 5/2015 | Ingimundarson et al. | |
| 2015/0216536 A1 | 8/2015 | Hopman et al. | |
| 2016/0022277 A1 | 1/2016 | Eikman | |
| 2017/0035440 A1* | 2/2017 | Hopman | A44B 11/20 |
| 2017/0100131 A1 | 4/2017 | Olbu | |
| 2018/0193030 A1* | 7/2018 | Ward | A61B 17/1325 |
| 2018/0271541 A1* | 9/2018 | Figueiredo | A61B 17/1327 |
| 2019/0021744 A1* | 1/2019 | Will | A61B 17/1327 |
| 2019/0247054 A1* | 8/2019 | Fostad Moe | A61B 17/1325 |
| 2020/0367909 A1* | 11/2020 | Rankins, III | A61B 17/1325 |
| 2021/0275191 A1* | 9/2021 | Ward | A61B 17/1327 |
| 2022/0039805 A1* | 2/2022 | Hsiao | A61B 17/1327 |
| 2022/0151638 A1* | 5/2022 | Fostad Moe | A61B 17/1327 |
| 2022/0313276 A1* | 10/2022 | Rankins, III | A61B 17/1327 |
| 2023/0140282 A1* | 5/2023 | Paulsen | A61B 17/1327 606/203 |

OTHER PUBLICATIONS

International Preliminary Report on Patentability in International Application No. PCT/NO2017/050229, dated Mar. 19, 2019.

Office Action in related Israeli Patent Application No. 265368, mailed on Sep. 8, 2022.

* cited by examiner

TOURNIQUET

CROSS REFERENCE TO RELATED APPLICATIONS

This application claims priority, as appropriate, to U.S. Ser. No. 16/333,222, titled "TOURNIQUET" and filed Mar. 13, 2019, which claims priority to PCT/NO2017/050229, titled "TOURNIQUET" and filed Sep. 15, 2017, which claims priority to Norwegian Patent Application No. 20161471, titled "TOURNIQUET" and filed Sep. 15, 2016, and to PCT/NO2021/050118, titled "TOURNIQUET" and filed May 7, 2021, which claims priority to U.S. Ser. No. 63/022,055, titled "TOURNIQUET" and filed May 8, 2020, the disclosures of which are hereby incorporated by reference in their entireties.

BACKGROUND

A tourniquet is useful for medical and therapeutic treatment of an injured individual. Tourniquets function by constricting an extremity in such a way that the blood flow is occluded. This provides a way for medical personnel and first responders to stabilize the patient in a pre-hospital setting, often at the site of injury. The tourniquet has seen extensive use in modern warfare and has, after the experiences of the U.S. and British military in Afghanistan and Iraq, gained recognition as a life-saving instrument. Tourniquet devices have become part of the personal equipment of U.S. forces and the demanding situations arising in combat means that the equipment must adhere to a number of specifications. Among the top priorities is the safety of use as well as ease of use. The equipment must be readily available and operational to personnel without medical training. Sophisticated equipment is difficult to use in extreme situations such as after terror attacks and in war and there is a need for a tourniquet which is robust in use and easy to handle.

Other considerations include weight and durability. Contrary to surgical tourniquets which utilize pneumatic systems to attain the necessary occlusion pressure, tactical tourniquets are often wholly mechanical in nature due to concerns of durability and reliability. In modern conflict there is an increasing threat from improvised explosive devices and with the added threat from terrorist organizations this has become a concern in urban environments such as major cities as well. If injuries occur due to explosives a tourniquet needs to be available within a convenient range of time and space. Tourniquets used outside a hospital are relevant to the military setting, but also as part of the civilian emergency response such as in accidents and terroristic attacks affecting civilians.

Different types of tourniquets have been developed for use in these cases. There are several disadvantages of many of the known tourniquets such as lack of robustness, lack of possibilities for controlled adjustments of the constriction, afforded power in the constriction, time used for the constriction as well as effectiveness and ease in handling the tourniquet by non-medical and medical persons potentially exposed to extreme situations.

US 2005/0627518 describes a tourniquet with a tensioning mechanism where the tension is adjusted by rotating a worm gear. A disadvantage of this tourniquet is the time taken to achieve occlusion due to a slow adjustment mechanism.

In US2012/0215254A1 a tourniquet is described with a tensioning mechanism with a buckle and pulley assembly. One disadvantage of this tourniquet is a problematic use with one arm.

U.S. Pat. No. 8,652,164B1 describes a tourniquet with a ratchet mechanism for tensioning the tourniquet. A disadvantage of this tourniquet is a cumbersome operation.

US 2011/024719A1 describes a tourniquet with a clamp for tightening the tourniquet. A disadvantage of this tourniquet is a problematic use with one arm.

US2016/0022277A1 describes a tourniquet with pull strap for tightening of the tourniquet. Also this tourniquet is problematic to use with one arm only.

Thus, there is a need for an improved tourniquet which overcomes the above mentioned problems and disadvantages.

SUMMARY

In general terms, this disclosure is directed to a tourniquet. In one possible configuration and by non-limiting example, a tourniquet includes a strap and a tensioning device having an arbor, a pull-cord, a pull-cord reel, and a gear system for translation of rotations from the pull-cord reel to arbor to increase tension in the strap.

The inventor has appreciated that the known tourniquets exhibit one or more problems in operation, for example:
(a) rapid adjustment of the tension to constrict bleeding is difficult,
(b) the tightening mechanism responds slowly to and converts poorly force applied by the operator to tightening of the tourniquet,
(c) pinching of the skin when tightening the tourniquet,
(d) efficiently release of tension when needed to remove the tourniquet,
(e) flexibility in use on limbs with different circumference,
(f) robustness in different operation conditions,
(g) non-intuitive use of the tensioning mechanism,
(h) complex and expensive to manufacture,
(i) lack of possibility to release or adjust constriction,
(j) regulation of maximum constriction to avoid injuries, and
(k) excess slack in the strap when the tourniquet is initially placed on a limb may cause delay, injury, or misuse.

The inventor has therefore devised a tourniquet capable of addressing one or more of the problems described in (a) to (k) above.

Thus, an object of the present disclosure is to provide an improved tourniquet that provides occlusion in an efficient manner, within short time and without the need for high forces during constriction.

Another object of the disclosure is to provide a tourniquet that may be operated by one hand only.

Yet another object of the disclosure is to provide a tourniquet that may be operated by two hands, providing more force available for efficient occlusion.

Yet another object of the disclosure is to provide a tourniquet that may be operated by one or two hands and where the operator can push against the limb for more efficient occlusion.

Yet another object of the disclosure is to provide a tourniquet that is fool proof and easy to operate, providing the required occlusion within seconds of time.

Yet another object of the disclosure is to provide a tourniquet that is flexible in use, providing possibility to encircle limbs with different diameter.

Yet another object of the disclosure is to provide a tourniquet that is robust, providing fewer exposed parts.

Yet another object of the disclosure is to provide a tourniquet that is safe to use, limiting the damages to the limb where the tourniquet is applied.

Yet another object of the disclosure is to provide a tourniquet that is more efficient and less expensive to manufacture.

Yet another object of the disclosure is to provide a tourniquet that is small and lightweight.

Yet another object of the disclosure is to provide a tourniquet which is easy to release and/or adjust in constriction.

Yet another object of the present disclosure is to provide a tourniquet that is usable in situations with limited space or access to the injured person.

Yet another object of the disclosure is to provide a tourniquet which allows for simple and quick mechanism to correct excess slack during an initial tightening of the tourniquet and a mechanical advantage to further tighten the tourniquet.

One or more of the objects and advantages are achieved by a tourniquet as defined in the independent claims. Additional embodiments are also defined in the dependent claims.

One aspect is a tourniquet comprising: a tensioning device that includes a housing and a pull-cord assembly; and a strap that passes through the housing, the strap having a first end and a second end, the strap being arranged to together with the housing form a loop for encircling a limb; wherein the pull-cord assembly is configured to advance the strap through the housing to tighten the loop. The tourniquet may further include a driving arbor enclosed at least partially within the housing and a secondary arbor enclosed at least partially within the housing, wherein the strap passes between the driving arbor and the secondary arbor as the strap passes through the housing.

Another aspect is a tourniquet comprising: a strap having a first end and a second end; and a tensioning device including: a housing; a driving arbor for advancing the strap through the housing to increase tension in a loop formed with the strap; an attach mechanism configured to affix the second end of the strap to the housing; a pull-cord and a pull-cord reel, the pull-cord being configured to provide rotations to the pull-cord reel; a coupling assembly for transferring rotations from the pull-cord reel to the driving arbor, and a locking mechanism to prevent release of the strap.

Yet another aspect is a tourniquet comprising: a strap having a first end and a second end; and a tensioning device including: a driving arbor; a pull-cord reel and a pull-cord for providing rotations to the pull-cord reel; and a gear system for translation of rotations from the pull-cord reel to the driving arbor, wherein the rotations of the driving arbor cause a loop formed in the strap to increase in tension.

Another aspect is a method of using a tourniquet comprising: encircling a limb/extremity with a loop formed with a strap of the tourniquet, wherein the strap passes through a housing of the tourniquet; pulling a first end of the strap to remove slack in the loop; and further tightening the loop by pulling a pull-cord of the tourniquet.

According to the present disclosure, it is provided a tourniquet comprising: a strap having a first and a second end for encircling a limb, and a tensioning device comprising a housing wherein the housing comprises: at least a first arbor for attaching and winding up the first end of the strap, a fastening means for affixing the second end of the strap to the housing, a rotation generating means for providing rotations for winding in the strap, a coupling for transferring of rotations from the rotation generating means to the arbor, and a locking mechanism to prevent unwinding of the strap. The rotation generating means of the tourniquet comprises a pull-cord for providing rotations for winding in the strap on the arbor. A main advantage of this tourniquet is the possibility of a fast linear constriction of the strap within a short time. The pull-cord can be operated by one hand and can be drawn in different directions without affecting the constriction.

Attaching the first end of the strap to the arbor comprises both a solution where the first end is directly attached to the arbor and a solution with an adjustable attachment for securing the strap to the arbor at a distance from the free end of the first end of the strap. This can for example be done by passing the strap through an opening in the arbor where the arbor has a braking mechanism preventing reverse movement of the strap. This allows pre-tensioning the tourniquet by hand before constriction via the rotation generating means.

Fastening means for affixing the second end of the strap to the housing may include locks, belts, buckles and similar being suitable for and having the purpose to fasten the second end of the strap to the housing. The fastening means is advantageous in providing a solution for rapid affixing when wrapping the strap around a limb before tightening the tourniquet. The fastening means may also be used as a rapid way to release the tourniquet by detaching the second end from the housing.

By rotation generating means it is also meant a swivel, a wheel, an electrical motor or other suitable means for outputting rotations.

By coupling it is also understood to mean a coupling that transfers rotations from the rotation generating means to the arbor. The coupling may be wheels, gears, belts, sprocket wheels, friction belts, hydraulic fluid transmissions, clutch mechanisms and the like. The coupling is advantageous in that it provides the possibility to increase or decrease the gear ratio, thereby allowing an improved transmission of force impact. Furthermore, it makes it possible to have a distance between the generation means for rotations and the arbor, also allowing the rotation generating means and the arbor to be arranged such that the rotation generating means and the arbor are not parallel.

Non-limiting examples of the rotation generating means include a pull-cord reel, which may include a mechanism for recoiling the pull-cord on the reel. The advantage of the recoil reel is that the pull-cord can be pulled repeatedly.

The locking mechanism may be releasable for unwinding the first end of the strap. This makes it possible to remove the tourniquet, adjust the tension and to easily check whether the tourniquet is still needed to stop bleeding.

The coupling may comprise a gear system for transmission of rotations from the reel to at least the first arbor. This has the great advantage that the force needed to constrict the tourniquet can be sufficiently lower. Many of the known tourniquets afford a high degree of force to be constricted and to stop the blood circulation. Using a gear system overcomes this problem. In some embodiments, the gear ratio between the reel and the arbor is at least 2:1 (e.g., at least 3:1). This will reduce the required force significantly.

The tension device can comprise a release system suitable for disengaging the pull-cord reel from at least the first arbor. This would allow the pull-cord to be rewound on to the reel without rotating the arbor.

In another embodiment the fastening means comprises a second arbor for winding up the second end of the strap whereby the second arbor is connected via an additional coupling to the rotation generation means. One advantage of two arbors is that the speed for tightening of the tourniquet is improved.

The locking mechanism may be configured to prevent further tensioning above a certain threshold level of the tension applied to the limb. For example, the locking mechanism may prevent the arbor form rotating when the tension is at or above the threshold level. This has the great advantage that damages due to a too high constriction of the strap around the limb may be avoided. Thereby a fast constriction is possible without damaging the limb due to high forces used during the constriction process.

The strap may be made of a smart textile for indicating tension applied to the limb. This has the advantage that the degree of constriction can be signalized to the user when the tourniquet is constricted around a limb and during the constriction process.

In another embodiment of the tourniquet, the tourniquet comprises a release mechanism for preventing the tourniquet being tensioned above a certain threshold tensioning degree, such as no more than 600 mm Hg. The release mechanism may prevent further tightening of the tourniquet when the certain threshold is met or exceeded by, for example, disconnecting the pull-cord reel from the arbor. This may be advantageous in avoiding damaging the skin or tissue being constricted.

The rotation of the arbor may be controlled by a spring-loaded ball lock mechanism. An advantage of a spring-loaded ball lock mechanism is rapid release and locking for adjusting of the occlusion provided by the tourniquet.

In yet another embodiment of the tourniquet, a rotation axis of the at least one arbor is perpendicular to a rotation axis of the pull-cord reel. One advantage of this is allowing a larger pull-cord reel without increasing the height of the housing.

In yet another embodiment of the tourniquet, the arbor comprises an opening for passing a free end of the first end of the strap through the opening. The opening may be provided longitudinally in the arbor. This is advantageous in allowing rapid initial tensioning of the tourniquet. Beneficially, because the strap is wound around the arbor, the length of the free end of the strap may be reduced, lowering the chances that the free end of the strap may tangle, catch on external equipment, or otherwise interfere with the effective use of the tourniquet.

In another aspect, the tourniquet may be used in a medical treatment. The tourniquet can be used to control and stop venous and arterial blood circulation to an extremity for a period of time. The strap of the tourniquet may be arranged around a limb/extremity and thereafter constricted by pulling the pull-cord to wind up the strap on the arbor.

In the disclosed tourniquets, the translation ratio from the reel to the arbor via the gear system is chosen such that one rotation of the reel results in one or more rotations of the arbor (e.g., a ratio of 1:3). This ratio may be preferred in cases where it would be advantageous to provide more rapid tightening of the tourniquet. In some embodiments of the tourniquet, the translation ratio is chosen such that one rotation of the reel results in less than one rotation of the arbor (e.g., a ratio of 2:1 or 3:1). The advantage of this ratio is that less pull force is needed for tightening of the tourniquet.

The length of the pull-cord in the disclosed tourniquets may be chosen in such a way that it can easily be operated single handed (e.g., if the user is the injured person himself/herself). For example, the pull-cord may have a length of 20 cm to 60 cm to be pulled using only one arm. The pull-cord may be shorter than 20 cm to allow a smaller dimension of the pull-cord reel. The pull-cord may be longer than 60 cm to allow an operator to apply more force to the arbor in a single movement. The pull-cord handle may be configured for operation by one hand and/or two hands. In circumstances where there is not sufficient space for the full length of the pull-cord to be pulled, this can be compensated by pulling the pull-cord multiple times to attain the same constriction as pulling the full length of the pull-cord.

In at least some embodiments, the strap to be placed around a limb may be fabricated from a lightweight and strong material, such as polyester or nylon webbing, with a width of 3 cm to 10 cm. For example, the strap may be 5 cm wide. Other material may also be employed, such as strong or reinforced synthetic fibers, textiles (woven or non-woven), leather, and cloth. In the context of this disclosure, strong material should be interpreted as a material that is suitable to sustain the tension needed to constrict bleeding from a wound.

The strap may also be wholly or partly be made from a smart textile as described in more detail in the following sections.

The details of one or more aspects are set forth in the accompanying drawings and description below. Other features and advantages will be apparent from a reading of the following detailed description and a review of the associated drawings. It is to be understood that the following detailed description is explanatory only and is not restrictive of the claims.

DETAILED DESCRIPTION

Figure 1:
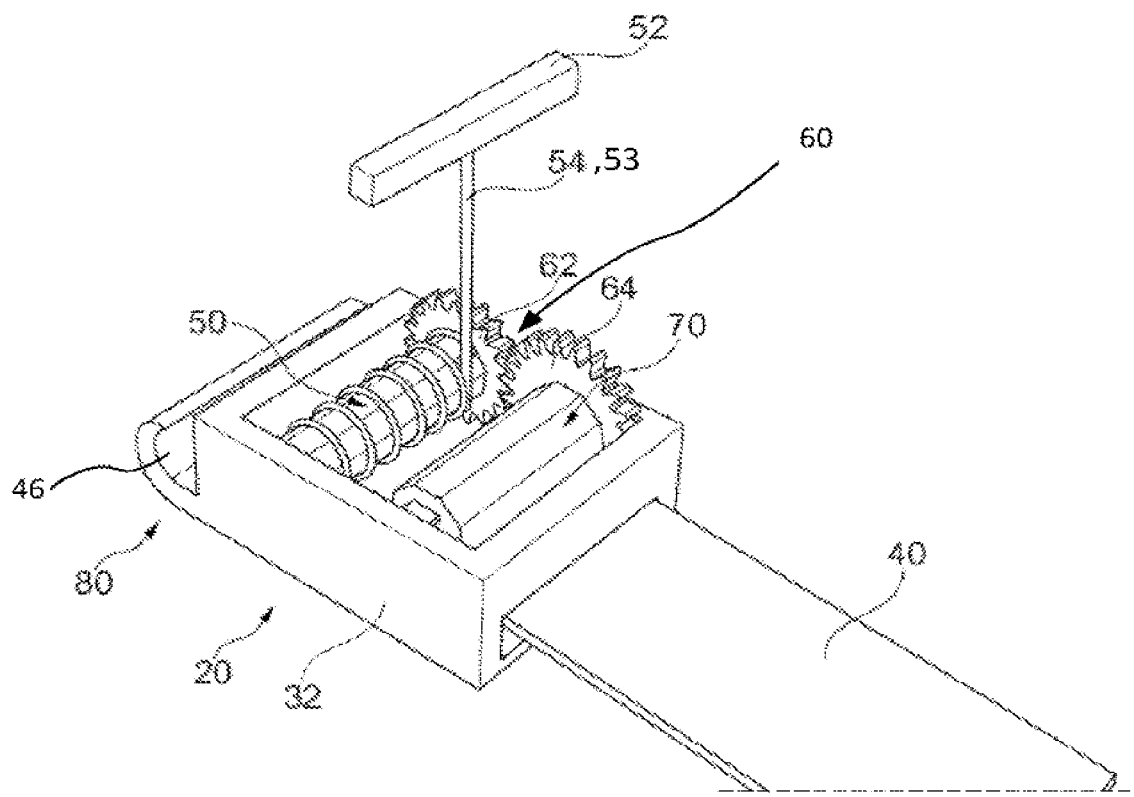
FIG. 1 shows schematically a perspective view of a tensioning device according to a first embodiment.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The following description of the example embodiments refers to the accompanying drawings. The same reference numbers in different drawings identify the same or similar elements. The following detailed description does not limit the disclosure.

Instead, the scope of the disclosure is defined by the appended claims. The following embodiments are discussed, for simplicity, with regard to various forms of tightening devices used in connection with a tourniquet. It should be appreciated, however, that the referenced tightening devices and systems are also applicable and suitable for use in respect to any other type of tourniquet and applications apart from use in the field. Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment.

As used in this disclosure, the term limb includes an extremity of a human or animal such as, but not limited to, a finger, hand, foot, leg, arm, also including parts of extremities.

The use of clockwise or counterclockwise in this disclosure is only for the purpose of illustrating a rotational direction. It is not meant as limiting the disclosure to only relating to the specified direction of rotation of the component. The direction of rotation of the rotating components may be arranged differently without departing from the scope of the disclosure.

The disclosure relates to a novel tourniquet, where tightening of the tourniquet is performed by linear motion by pulling a pull-cord. The tourniquet comprises a tensioning device and a strap. The first end of the strap is coupled to the tensioning device. The second end of the strap is wrapped around a limb and also fixed to the tensioning device. The tightening of the tourniquet is achieved by pulling the pull-cord. Linear motion by the pull-cord is translated into winding up the strap inside the tensioning device, and thereby tightening the tourniquet. Embodiments of tourniquets according to the present disclosure may further comprise a release mechanism that provides possibility to readjust or release the tightening of the tourniquet. Furthermore, embodiments may comprise elements suitable to limit the maximum level of possible tightening.

FIG. 1 shows a first embodiment of a tensioning device 20 (which may also be referred to as a tension adjustment device). In FIG. 1 a base or housing 32 and a section of a strap 40 are shown. The strap 40 is fixed with a first end (not shown) to an arbor 70 mounted inside the base. In operation the strap 40 is tightened in a loop around an injured limb and fixed with the other (second) end (not shown) of the strap 40 to the other side of the base (not shown) e.g. by a quick lock hook 80. For the purpose of describing the tourniquet, the tensioning device 20 is shown without a cover. The base 32 provides support for the working mechanics for the tensioning device 20. A pull-cord recoil reel 50, where the pull-cord 54 is rolled up on the reel 50, is located inside the base 32. The reel 50 is internally coupled to the base 32 and may rotate around its longitudinal axis. A first gear wheel 62 is provided at an end of the reel 50. An arbor 70, whereto the first end 42 of the strap 40 is affixed and on which the strap 40 can be wound up during the tensioning procedure, is located inside the base 32 and can rotate around its longitudinal axis. The arbor 70 and the reel 50 are arranged in parallel along their longitudinal axis. A second gear wheel 64 is provided on the arbor 70. The first gear wheel 62 and the second gear wheel 64 are arranged in such a way that they mesh with each other and that their rotational axis is parallel for transfer of the rotational movement from the pull-cord activated reel 50 to the arbor 70 with the affixed strap 40. Thus, the gear wheel arrangement is such that rotations of the reel 50 are translated to rotations of the arbor 70 via the gear wheels 62, 64 provided on each of the rotatable reel 50 and arbor 70. The strap 40 is secured to the arbor 70 and clockwise rotations of the arbor 70 will wind the strap 40 up on the arbor 70. The first end 42 of the strap 40 may be secured to the arbor 70 by gluing, welding, stitching or similar. The first gear wheel 62 and the second gear wheel 64 may have a conversion ratio of 3:1, where three complete rotations of the first gear wheel 62 are translated to one complete rotation of the second gear wheel 64. Such a conversion ratio will result in three times more tightening force applied to the strap for constriction than the linear force applied by pulling the pull-cord. Thereby an easier tightening of the tourniquet is achieved resulting in a particularly efficient constriction to stop venous and arterial blood circulation to an extremity.

In embodiments of the disclosed tourniquets, the translation ratio from the first gear wheel 62 to the second gear wheel 64 may be chosen such that one rotation of the first gear wheel results in one or more rotations of the second gear wheel (e.g., a ratio of 1:3). This translation ratio may be advantageous to provide more rapid tightening of the tourniquet. In other embodiments of the tourniquet, the translation ratio from the first gear wheel 62 to the second gear wheel 64 may be chosen such that one rotation of the first gear wheel results in one or more rotations of the second gear wheel (e.g., at a ratio of 3:1). The advantage of this ratio is that less pull force is needed for tightening of the tourniquet.

The length of the pull-cord in the disclosed tourniquets may be chosen in such a way that it can easily be operated single handed (e.g., if the user is the injured person himself/herself). The pull-cord may have a length of 20 cm to 60 cm to be pulled using only one arm. The pull-cord may be shorter than 20 cm to allow a smaller dimension of the pull-cord reel. The pull-cord may be longer than 60 cm to allow an operator to apply more force to the arbor in a single movement. The pull-cord handle may be configured for operation by one hand and/or two hands.

A quick lock hook 80 for attachment of the second end of the strap 40 is shown in FIG. 1. A corresponding quick lock hook (not shown) is provided on the free (second) end 44 of the strap. A quick lock assembly is formed when the two quick lock hooks engage with each other for fastening the free end of the strap to the base.

In another embodiment the quick lock hook 80 for attachment of the second end of the strap 40 may be shaped to correspond to the second end of the strap. The corresponding end of the strap may be molded in such a way that it slides sideways into the quick look hook and fixes the second end of the strap in the quick lock hook 80.

The tourniquet shown in FIG. 1 may be packaged in a disposable bag for protection and storage. Use of the tourniquet is performed by placing the tensioning device 20 on a limb (not shown) or an extremity above the bleeding wound. The strap 40 is wrapped around the wounded limb and the second free end of the strap 40 is secured to the quick lock hook 80. The quick lock assembly may provide some means for "gross" cinching tension of the tourniquet. The subsequent tightening of the tourniquet for constricting of the blood circulation is achieved by an operator pulling the handle 52 of the pull-cord 54. The thereby achieved linear motion of the pull-cord 54 will translate to linear tension of the strap 40 around the limb when the arbor 70 rotates.

The gear wheel arrangement 62, 64 may additionally comprise rotation locking means (not shown) to restrict unwinding of the strap 40 wrapped up on the arbor 70. These rotation locking means may be locking arms, friction brakes, or similar means that prevent undesired unwinding of the strap 40. Alternatively, locking means for locking the rotational movement of the reel 50 and/or the arbor 70 may be provided directly on the reel 50 and/or the arbor 70.

In other embodiments the gear wheel arrangement may comprise additional intermediate gear wheels. Rotations of the first gear wheel 62 may be translated to rotations of the second gear 64 wheel via one or more intermediate gear wheels. An advantage with additional gear wheels is to allow a longer distance between the recoil reel 50 and the arbor 70 as well as a high translation of rotational movements.

In other embodiments the arbor 70 may have a slot where the free end of the first end of the strap can be entered through. This will give the possibility to apply gross cinching to the limb by the strap 40 before the rotation of the arbor 70 further tightens the tourniquet 10.

Figure 2:
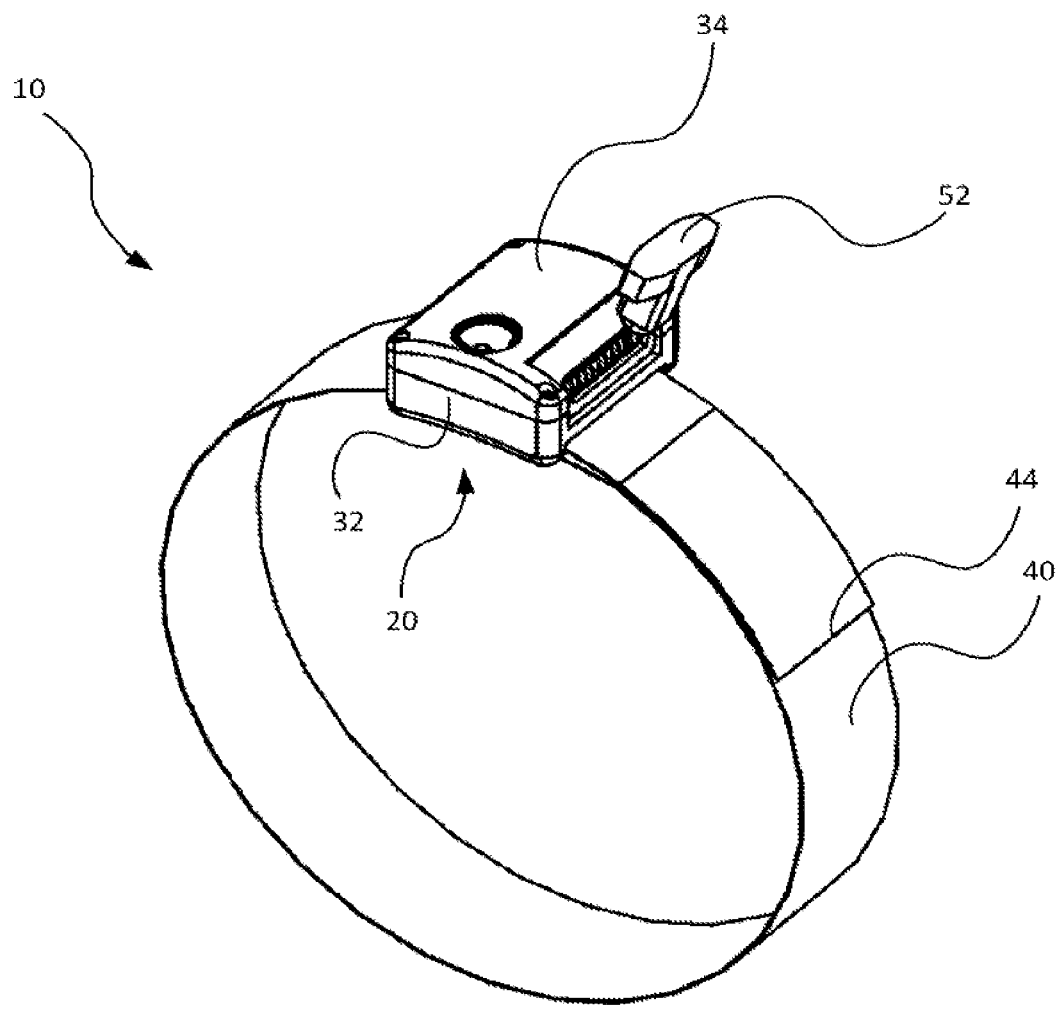
FIG. 2 shows schematically a perspective view of a tourniquet of a second embodiment according to the present disclosure indicating an assembled tourniquet.

A second embodiment of a tourniquet 10 is shown in FIG. 2. As described above for the first embodiment, the tourniquet 10 comprises a strap 40 to be circumferentially arranged around an injured limb (not shown) in order to stop the flow of blood when constricted. The tourniquet 10 is designed to prevent blood loss in a patient's limb through the application of pressure to constrict the severed blood vessel. The tourniquet 10 further comprises a tension adjustment device 20 and mechanism which is coupled to the strap 40 on each side for constricting of the strap 40 after being placed around the limb. The tension adjustment device and mechanism 20 may be placed inside a housing/base 32.

In at least some embodiments, the strap 40 is fabricated from a lightweight and strong material, such as polyester or nylon webbing, with a width of 3 cm to 10 cm, such as 5 cm width. Other material may also be employed, such as strong or reinforced synthetic fibers, textiles (woven or non-woven), leather, and cloth. In the context of this disclosure, strong material should be interpreted as a material that is suitable to sustain the tension needed to constrict bleeding from a wound. The tourniquet 10 may be designed to provide initial "gross" tension by cinching the strap 40 and finely adjusting the tension by manipulating the tension adjustment mechanism by means of the tension adjustment device 20.

Still referring to FIG. 2, the strap 40 has a first end (not shown) and a second end 44. The first end 42 is coupled to the tension mechanism inside the base/housing 32. The tourniquet is applied to a limb by wrapping the strap 40 around the patient's limb and securing and affixing the second end 44 of the strap 40 to the housing 32. The second end 44 may be detachable from the housing 32 and can be secured to the housing 32 by fastening means such as a quick attach mechanism e.g. as described for FIG. 1. A quick attach mechanism as described below has the advantage that the strap can be fastened and pre-tightened in a fast expedient and efficient one-step procedure. The feature of a detachable second end 44 of the strap 40 facilitates the positioning of the strap 40 around the injured limb as well as its removal. It is thus a more gentle procedure for the patient. Moreover, it allows a flexible use of the tourniquet 10 for different types of limbs having different circumferences, since the length of the strap 40 can easily and efficiently be adjusted to the length afforded for embracing the limb. In another embodiment (not shown), however, the strap 40 may be permanently fixed to the housing. In this case, the strap is pre-fixed in the form of a loop and has to be drawn over the limb for positioning. In this case, the circumference of the loop should more or less correspond to the circumference of the limb in order to facilitate the later constriction of the strap or it should be provided with a suitable adjustment mechanism to adjust the size of the loop.

Figure 3:
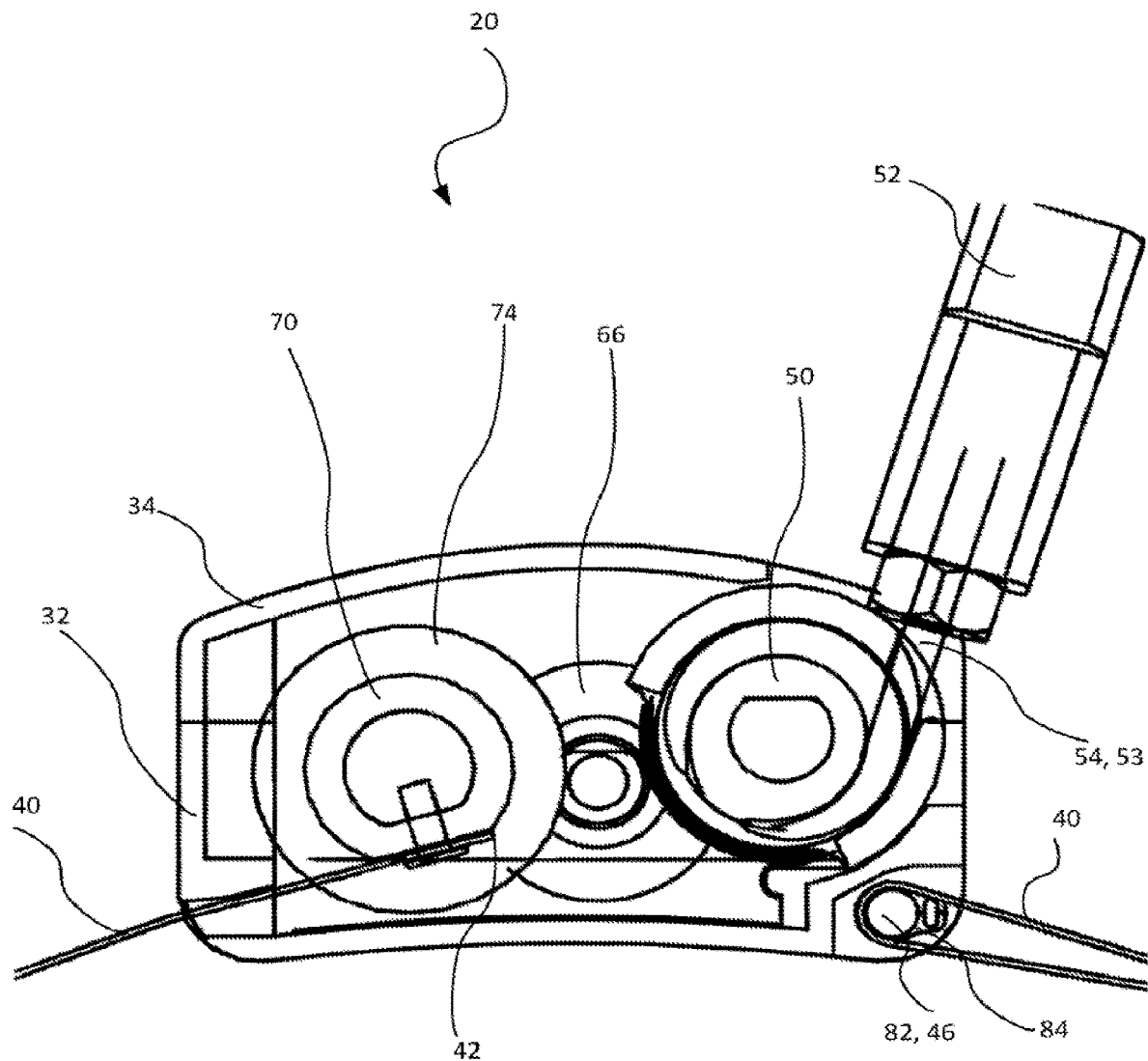
FIG. 3 shows schematically a cross section view from the side of the second embodiment according to FIG. 2.

A quick attach mechanism which may be included in at least some embodiments, is a Velcro™ buckle lock. FIG. 3 shows a cross sectional view of the tensioning device 20, where the second end 44 of the strap 40 is entered through an opening and looped around a lock cylinder 82 forming a loop. The lock cylinder 82 has at least a locking ring 84 that will prevent the strap 40 from any sideways movement. The strap 40 may comprise a Velcro™ fastener at the second end 44 of the strap 40 as well as with a corresponding section of Velcro™ on another area of the strap 40. When the second end 44 of the strap 40 is looped around the lock cylinder 82 the end of the second end 44 of the strap 40 may be secured to the Velcro™ section on the strap 40.

Another example of the quick attach mechanism includes a magnetic locking device. Such a magnetic locking device may comprise a first member that is coupled to the housing 32 and a second member that is attached or coupled to the second end 44 of the strap 40. The first and the second member can engage with each other to securely fasten the second end of the strap to the housing 32. The first member and the second member comprise at least one magnet and the first and second member are held together by magnetic attraction between the magnets. The first member and the second member may be releasably locked to each other and are used to connect the second end of the strap 40 to the housing 32. The second member may be provided with adjustment means for the initial "gross" tension by cinching the strap around the limb.

Other types of quick attach mechanism may alternatively be applied in any of the disclosed tourniquets, including, but not limited to, hook and loop, a seatbelt-type attachments, clips fasteners or similar. The quick attachment means are used to quickly and reliably secure the second end of the strap 40 to the housing.

The quick attach mechanism may provide adjustment means for the initial "gross" tension by cinching the strap around the limb. The initial gross tensioning is performed by tightening the strap through the self locking loop. It is advantageous to perform initial gross tensioning to reduce the strap that needs to be wound up inside the tensioning device.

Other types of gross cinching devices or techniques may alternatively be applied, including, but not limited to, hook and loop fastening material, a seatbelt-type clamping assembly, two-part adhesives, zip ties, Velcro™, etc.

The final adjustment of the tension is done by manipulating the tension adjustment mechanism. The manipulation of the tension mechanism is performed by pulling a handle 52 coupled to a pull-cord 54. Linear motion applied to the pull-cord 54 is thereby translated into linear motion applied to the strap 40 via the tensioning device 20. Pulling the handle 52 of the pull-cord 54 will increase the tension applied by the strap 40 wrapped around the limb.

In other embodiments the strap 40 may comprise several band sections, where at least a first section is coupled to the tension adjustment mechanism and there is provided means for coupling the additional sections together forming a continuous strap to be arranged around the limb. The strap 40 is then attached to a quick attach mechanism on the tension adjustment device 20. The strap 40 may comprise an adjustment means for adjusting the length of the strap 40. The adjustment means for shortening the strap can e.g. be double D-rings, Velcro™, loop-and-hook, and the like.

Figure 4:
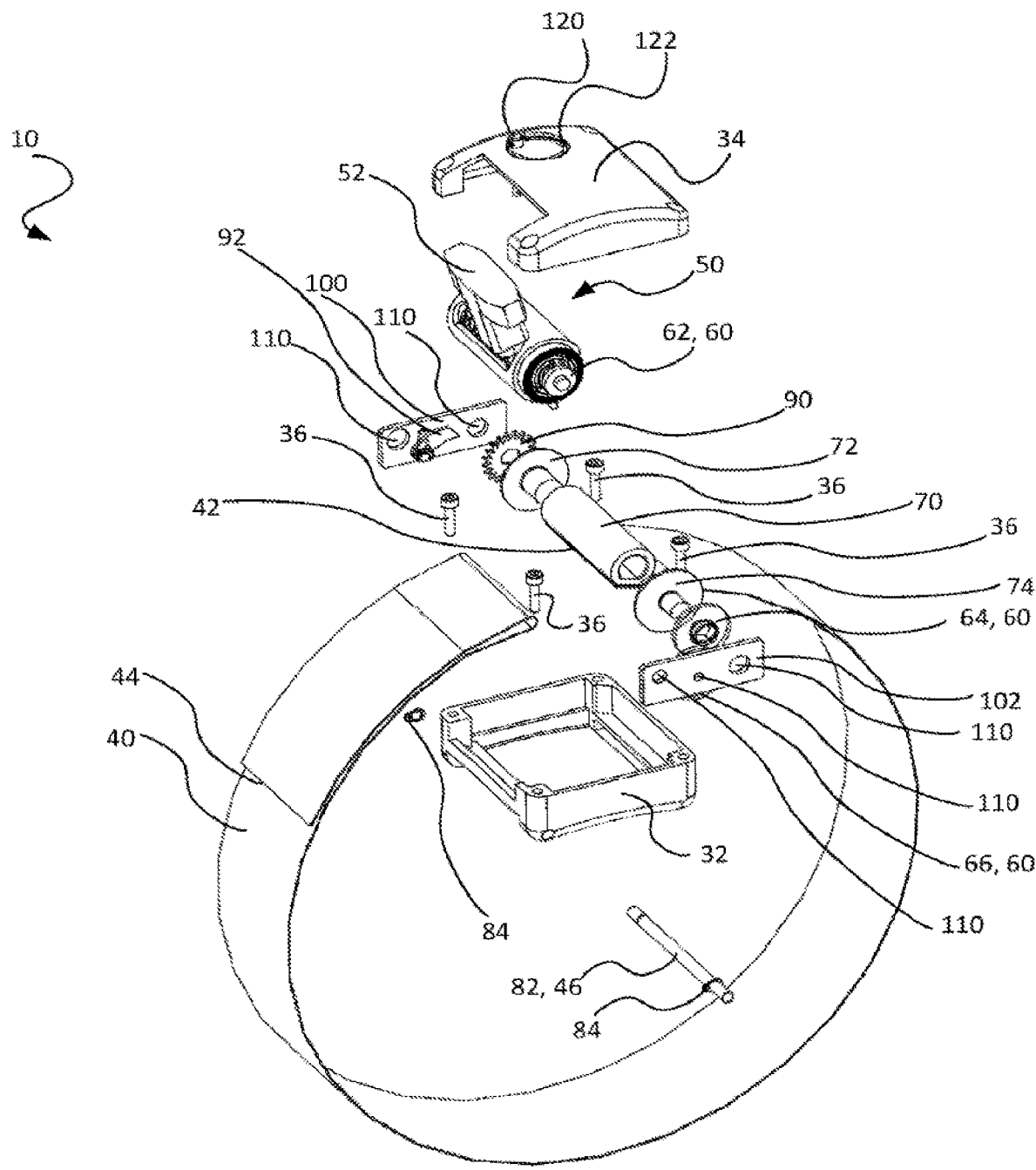
FIG. 4 shows schematically an exploded view in perspective of the second embodiment according to FIG. 2.

FIG. 4 shows an exploded view of the second embodiment of a tourniquet 10. The shown tourniquet 10 comprises a strap 40 and a tensioning device 20. The tensioning device 20 comprises a housing 32 which contains the working components of the tensioning device 20. The housing is in the form of a base 32 and has a corresponding cover 34. The base 32 and the cover 34 mate with one another, and are suitably attached, for example, by screw fasteners 36, to encase the working components of the tensioning mechanism. The attachment of the base 32 and the cover 34 may also be based on other suitable techniques such as bonding with adhesive, bonding by solvent, heat staking/welding, gluing, ultrasonic welding, and mechanical snap fasteners etc. The housing may be fabricated from lightweight, strong material, such as plastic, a lightweight metal and/or metal alloy, ceramics, or composites, also including combinations thereof.

Still referring to FIG. 4, the tensioning mechanism includes a spring-loaded recoil reel 50. The spring-loaded recoil reel 50 comprises a handle 52 attached to a second end of a pull-cord (not shown). The first end of the pull-cord is attached to the recoil reel 50 in the form of a cylinder. The pull-cord may be rolled up on the recoil reel cylinder prior to use. The recoil reel 50 may further comprise a rewind spring to rewind the pull-cord up on the reel. The rewind spring may be a flat spiral spring where the inner end is coupled to the cylinder and the outer end is secured to the base. When pulling the pull-cord, by means of the handle 52, linear motion of the pull-cord is translated to rotation of the recoil reel with the wound cord and attached second end of the cord. The linear motion of the pull-cord will tension the rewind spring. When the handle is released the rewind spring will rewind the pull-cord up on the reel 50. The rotation of the reel is further translated via a clutch mechanism (not shown in FIG. 4) to rotation of a first gear wheel 62, which is connected coaxially via the clutch mechanism to the recoil reel 50. A person skilled in the art would know how to construct a clutch mechanism that temporarily disengages the reel from the first gear wheel when the pull-cord is rewound up on the reel and this is therefore not explained in more detail. The recoil reel to be used in embodiments of the tourniquets may be fabricated in any suitable and lightweight material like plastic or metal or a combination of the two. The pull-cord may be made in a flexible, water resistant material which is able to sustain the forces acting upon it when pulling the pull-cord; some non-limiting examples are nylon, or metal wire.

The rewind functionality of the pull-cord may well be achieved by a suitable arrangement of a rubber band or other means coupled to the reel 50. After releasing the pull-cord, the pull-cord will rewind on to the reel.

The tensioning mechanism further comprises means for linearly shortening the strap 40. As shown in FIG. 4, the tensioning mechanism is in the form of an arbor 70. The first end 42 of the strap 40 is secured to the arbor 70. The arbor 70 has a first end and a second end along its longitudinal axis. A lock wheel 90 and a first spacer element 72 are coupled to the first end of the arbor 70. Similarly, a second spacer element 74 and a second gear wheel 64 are coupled to the second end of the arbor 70. The spacer elements 72, 74, the arbor 70, the lock wheel 90, and the second gear wheel 64 together form a unit that rotates together. The lock wheel 90 has the function to prevent unwinding of the arbor 70.

In some embodiments, the first end 42 of the strap 40 is secured to the arbor 70 by gluing, but may be affixed by stitching, welding or other suitable ways to secure a strap end to an object. In at least some embodiments, the arbor 70 is fabricated from any suitable material such as plastic or metal.

In some embodiments, the spacer elements 72, 74, the arbor 70, the lock wheel 90, and the second gear wheel 64 are separate parts, but may also be manufactured as an integral piece in the same material. These elements may be fabricated from any suitable material like plastic, or metal.

A first and a second holding bracket 100,102 are provided to fix the mechanic workings inside to the housing. The working mechanics comprise the arbor 70 with the spacer elements 72, 74, the lock wheel 90 and second gear wheel 64, the recoil reel 50 with the first gear wheel 62, and a third gear wheel 66. The holding brackets 100, 102 are provided with recesses 110 for accommodating protrusions on the longitudinal axis of the working mechanics. The holding brackets 100, 102 fix the arbor 70 and the recoil reel 50 in such a way that the arbor 70 and the recoil reel 50 are parallel. The second holding bracket is provided with recesses for fixing the first gear wheel 62, second gear wheel 64, and third gear wheel 66. The gear wheels 62, 64, 66 together form a gear system.

The gear system is adapted to translate the force applied by pulling the pull-cord (not shown) of the recoil reel 50 to linear motion applied to the strap 40. In the gear system, the first gear wheel 62 is rotated by the linear motion of pulling the pull-cord of the recoil reel 50. The first gear wheel 62 meshes with the third gear wheel 66. The third gear wheel 66 meshes with the second gear wheel 64. Rotations of the first gear wheel 62 are transferred to rotations of the second gear wheel 64, via the third gear wheel 66, at a ratio of 3:1. It is appreciated that the number of gear wheels may vary and can e.g. be more than three in other embodiments.

Figure 5:
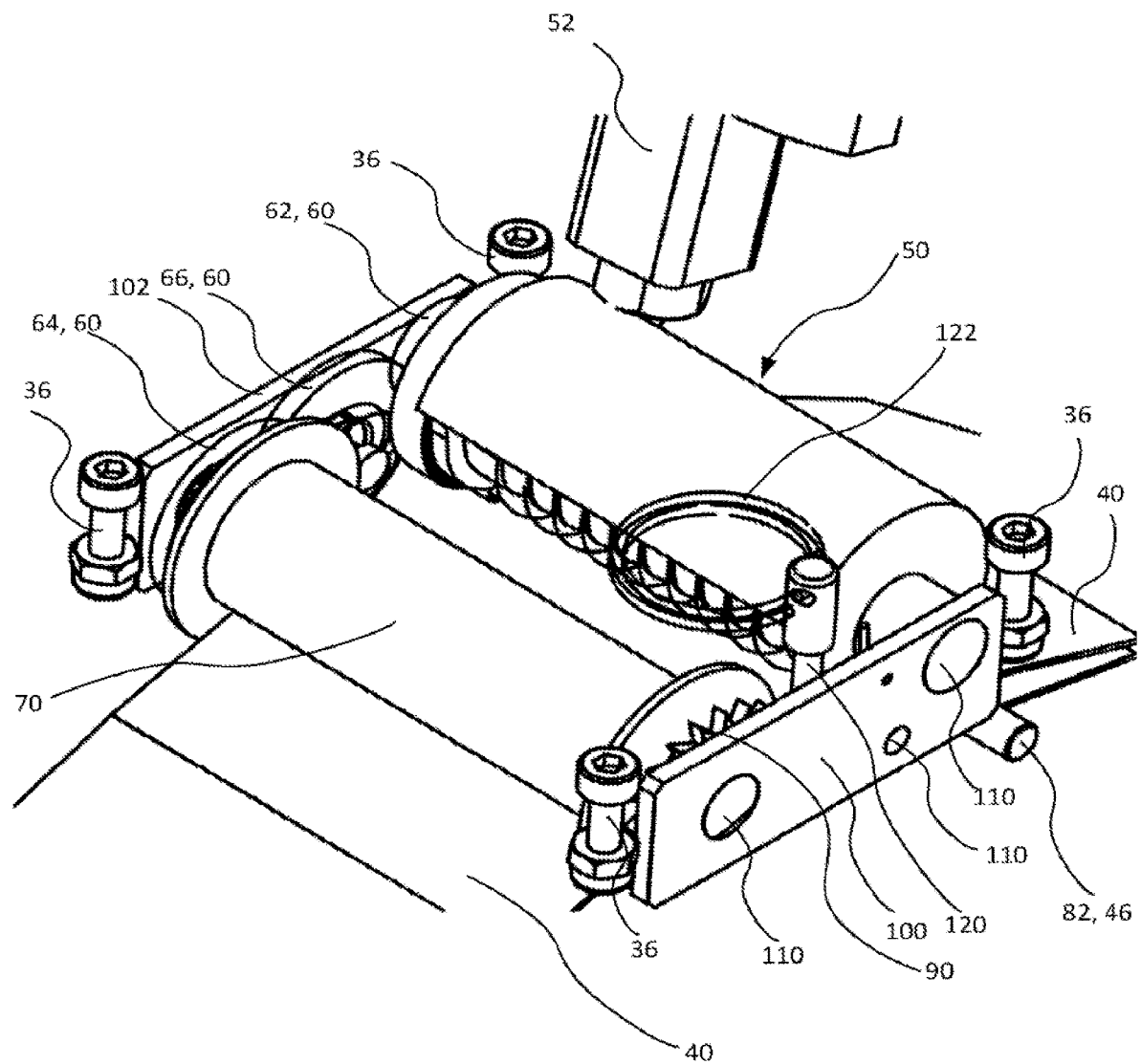
FIG. 5 shows schematically a perspective view of the mechanical workings of the second embodiment according to FIG. 2.

Referring to FIG. 5 the working mechanics are shown as fixed between the holding brackets 100, 102. The recesses 110 of the holding brackets 100,102 allow the arbor 70 and the recoil reel 50 to rotate around their longitudinal axis.

Referring to FIG. 4 the first holding bracket 100 further comprises a spring-loaded locking arm 92. The locking arm 92 engages with the lock wheel 90 and stops counterclockwise rotations of the arbor 70. The locking arm 92 and the lock wheel 90 form a locking arrangement for stopping unwinding of the strap 40 that is wound on to the arbor 70 during tensioning of the tourniquet 10. The locking arrangement will allow rotations of the arbor for winding up the strap. In some embodiments, the locking arrangement comprises the disclosed spring-loaded locking arm 92 and the lock wheel 90. In other embodiments the locking arrangement may be designed using friction brakes or other means that prevents unwinding of the strap on the arbor.

The brackets and the gear wheels may be made of a suitable lightweight and robust material like metals, plastics, ceramics, or composites.

In the embodiment shown in FIG. 4, the recesses 110 are circular holes through the flat surface of the brackets. In other embodiments the recesses may be only small cavities in the surface.

In some embodiments the gear system may be designed with friction gears, belts, worm gears, or other means to translate the linear movement applied by pulling the pull-cord, via the recoil reel, to rotational movement applied to the arbor.

In some embodiments, the gear system may have a gear ratio chosen such that one rotation of the reel results in one or more rotations of the arbor (e.g., a ratio of 1:3 or 1:2) to achieve more rapid tensioning of the tourniquet. It would in other embodiments be advantageous to have a gear ratio chosen such that one rotation of the reel results in less than one rotation of the arbor (e.g., a ratio of 2:1 or 3:1). This requires less linear force to be applied by pulling the pull-cord during tensioning of the tourniquet.

In FIG. 4 a release mechanism suitable for manual activation by an operator, is provided through a second opening in the cover 34. The release mechanism comprises a release pin 120 that engages with the locking arm 92. In place the release pin 120 will force the locking arm 92 to stop all counterclockwise rotation of the arbor 70. Removing the release pin 120 will disengage the locking arm 92 from the lock wheel 90 with the result that the arbor 70 is free to rotate in a counterclockwise direction and release the tension of the strap 40. The release pin 120, as shown in FIG. 4, is accessible from the outside of the assembled housing. Coupled to the release pin 120 is a ring 122, where the ring 122 makes it easier to get hold of the release pin 120.

In some embodiments the release mechanism may be made in such a way that the arbor can be relocked, e.g. by a push button coupled to a spring-loaded release pin that temporarily disengages the lock arm from the locking wheel.

During assembly of the tensioning mechanism, the arbor 70, the gear system 62, 64, 66, and the recoil reel 50 are held in place by the brackets 100,102 when fitted inside the base 32 and when the cover 34 is attached. The brackets 100, 102 are held in place by fitted slots in the base 32. The handle 52 of the recoil reel 50 will then be located externally to the housing. A schematically view of the mechanical workings of the second embodiment is shown in FIG. 5.

Figure 6:
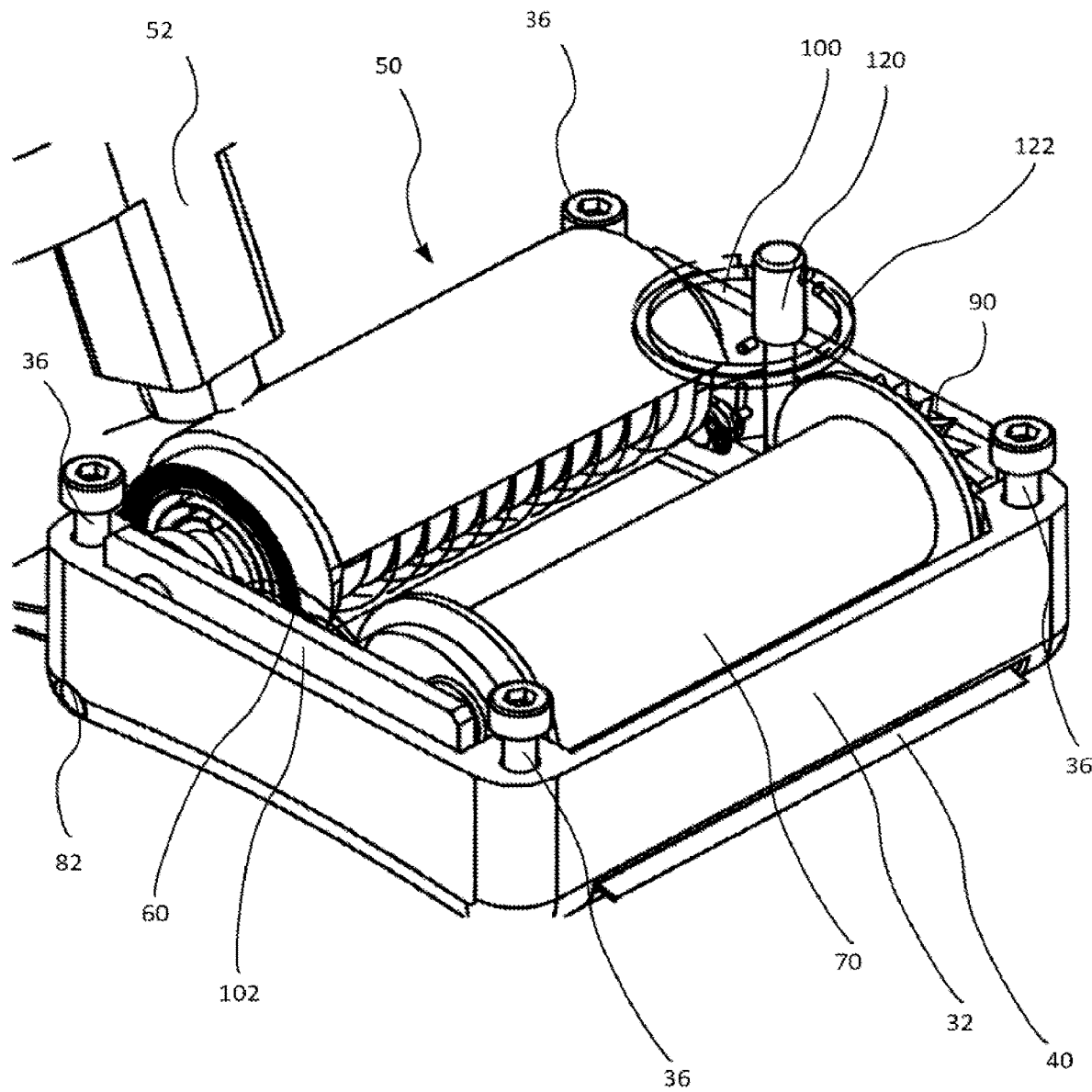
FIG. 6 shows schematically a perspective view of the housing of the second embodiment according to FIG. 2 without cover.

In FIG. 6 is shown a view of the housing of the second embodiment where the cover 34 has been removed. The brackets 102, 100 fix the arbor 70 and the recoil reel 50 inside the base 32. The strap 40 is entered through an opening in the base 32 and fixed to the arbor 70. Linear force applied by pulling the handle 52 is transferred to the arbor 70 via the gear wheel system and the strap 40 is wound up on the arbor 70.

Figure 7:
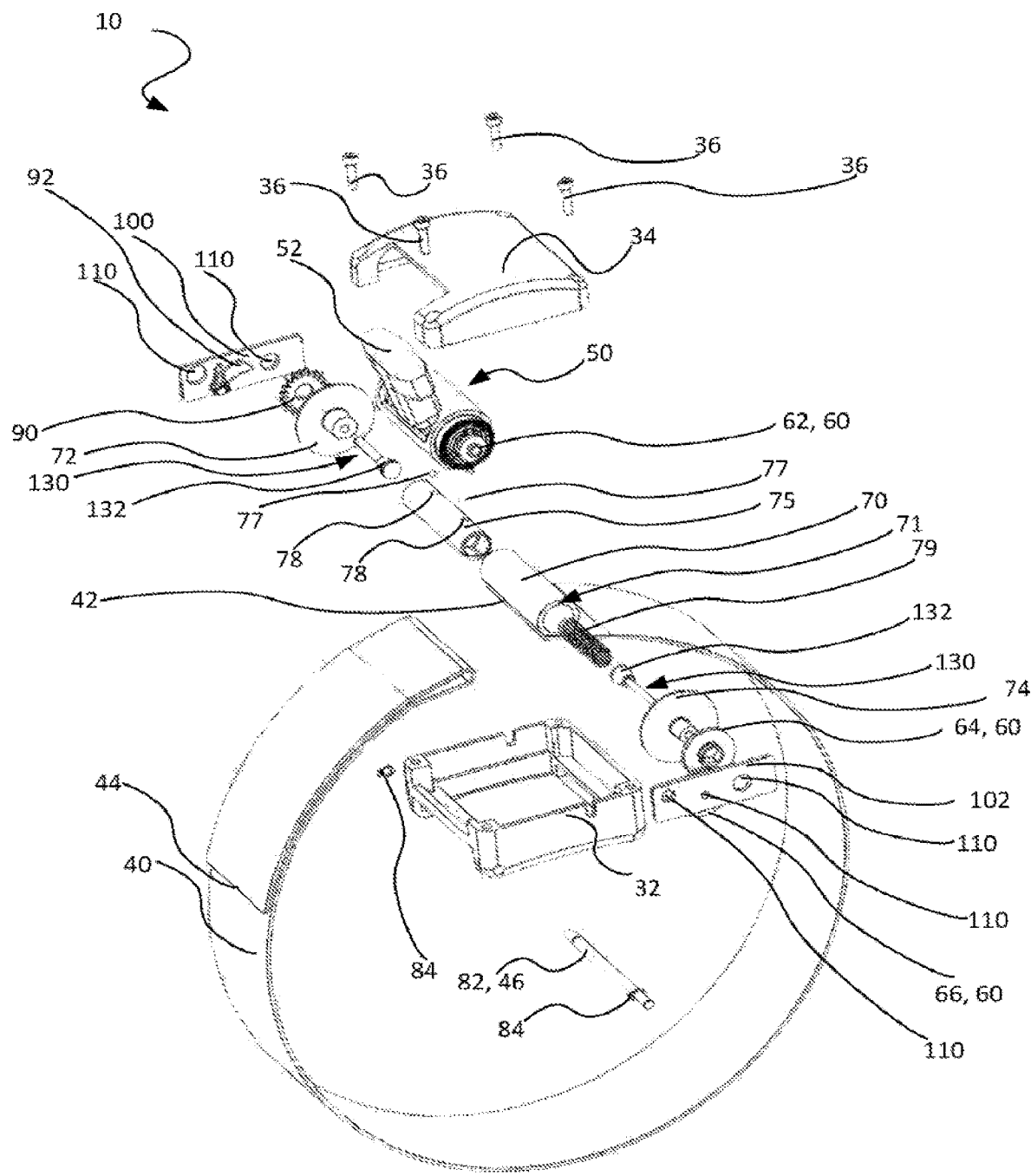
FIG. 7 shows schematically an exploded view in perspective from the side of a third embodiment.

In FIG. 7 is shown an exploded view of a third embodiment of a tourniquet. The third example embodiment of the tourniquet 10 corresponds to the second example embodiment apart from an alternative release mechanism for the arbor 70. Referring to FIG. 7, the release mechanism for the arbor 70 is a spring-loaded ball locking mechanism. The spring-loaded ball locking mechanism in addition to the arbor 70 comprises an inner cylinder 75 with two circular recesses 78, two balls 77, two push pins 130 and a spring 79. The inner cylinder 75 is dimensioned to fit inside the arbor 70. Inside the arbor 70 there is at least one longitudinal groove 71, suitable in size to engage with the two balls 77. The circular recesses 78 are on a common longitudinal axis of the inner cylinder 75 and are dimensioned such that whole or parts of the balls 77 can pass through. The two push pins 130 are provided with a cone shaped section 132 at a first end of each pin 130 facing towards the center of the arbor. Assembling of the arbor 70 with the spring-loaded ball locking mechanism is performed by placing the spring 79 inside the inner cylinder 75, the two push pins 130 are placed inside the inner cylinder facing with their coned shaped section 132 towards the central spring 79. One ball 77 is placed in each of the recesses 78 and is resting against the cone shaped section 132 of the push pins 130 in each end of the spring 79. The inner cylinder 75 with the two balls 77, the spring 79 and the push pins 130 are placed inside the arbor 70. The ball 77 engages with the inner groove 71 of the arbor 70 and secures the inner cylinder 75 to the arbor 70 and the arbor 70 and the inner cylinder 75 rotate together. The tourniquet 10 is otherwise assembled and constructed in similar fashion as previously described for the second embodiment. The push pins 130 from the release mechanism protrude through the base 32 through recesses in the side walls of the base 32. Pushing the push pins 130 by an operator towards the center of the longitudinal axis of the arbor 70 will disengage the balls 77 from the groove 71 due to a reduced diameter of the cone of the push pins, when dislocated by pushing them inwardly towards the center of the arbor 70. Thereby, the balls 77 are released from their position and the arbor is unblocked. The arbor 70 can now rotate more or less freely and release the strap 40 that is wound around the arbor 70. When the push pins 130 are released, they will be pressed into their starting position by the now expanding spring 79. Thereby the cone shaped sections 132 of the push pins 130 will press the balls through the recesses 78 of the inner cylinder 75 into the circumferential grooves 71 of the arbor 70 and the rotational movement of the arbor will be locked and hindered again from further rotations and unwinding.

The push pins 130 are suitable to release and/or to adjust the tension/constriction when the tourniquet is tensioned around a limb. The third embodiment of the tourniquet 10 is otherwise operated and applied to a patient similar to other known tourniquets and as principally described above for the first and second embodiment. The described locking mechanism has the great advantage that it is easy to release the tourniquet, for example, for checking whether the bleeding has stopped or in cases where the constriction is too high and causes pain. The described mechanisms allow releasing, adjusting, and reconstricting the tourniquet repeatedly without problems. Another advantage of the described release mechanism is that the tension in the spring 79 and angle of the cone shaped section 132 may be selected to disengage the balls 77 from the groove above a certain threshold tensioning degree of the tourniquet. It is considered that a tourniquet tension of more than about 600 mm Hg may inflict permanent damage to tissue and nerves. In some embodiments, the spring tension and cone angle may be selected to prevent the tourniquet from being tightened above a certain threshold tension level. In other circumstances, there may be a need for the release mechanism to release at a higher level, e.g., when the tourniquet is applied over clothes to make sure that the bleeding is properly stopped.

Figure 8:
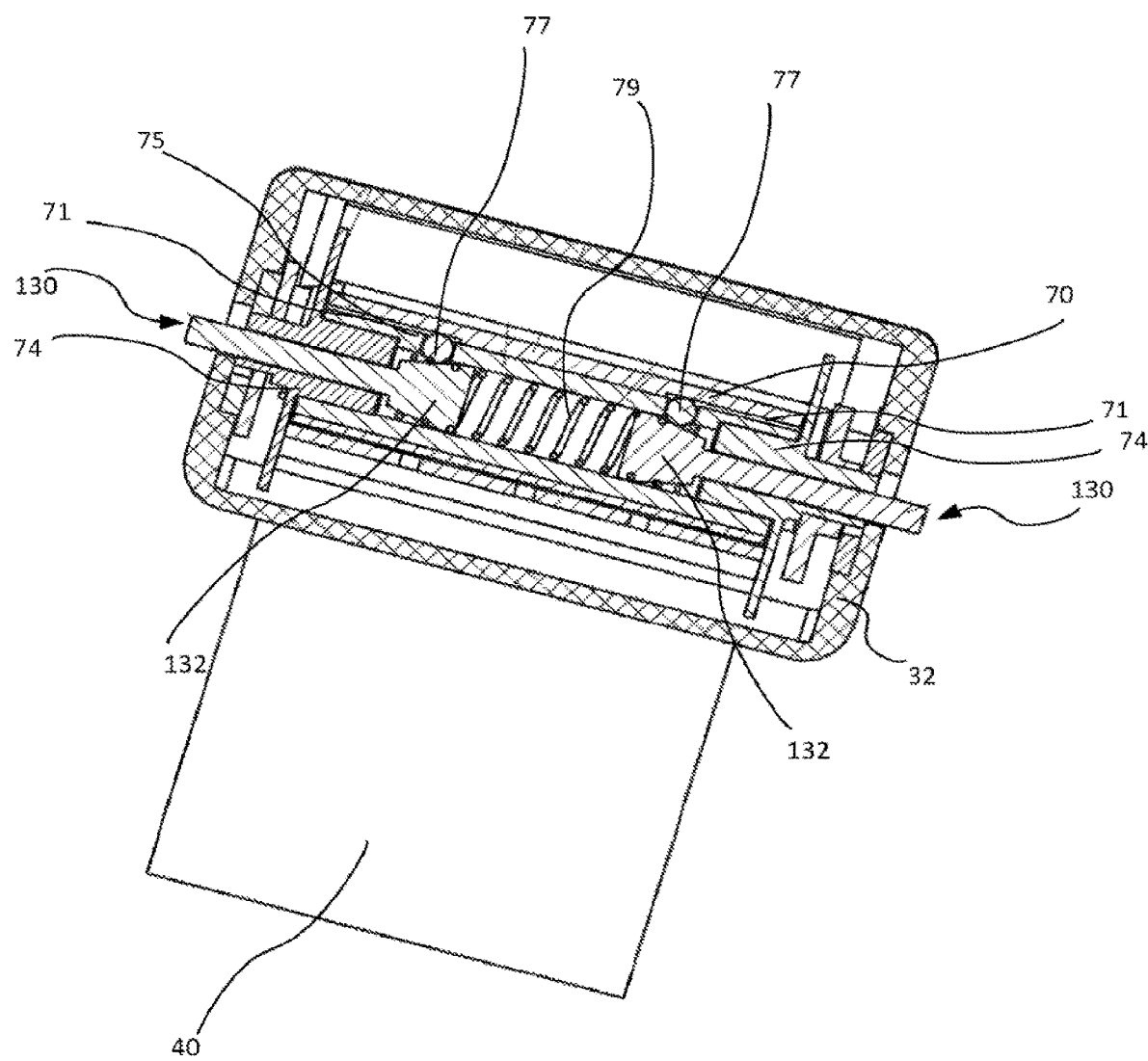
FIG. 8 shows a cross sectional view of the tension device of the third embodiment.

FIG. 8 shows a cross sectional view of the tension device of the third embodiment of the tourniquet 10. The housing 32 is surrounding the inner mechanics of the tensioning device. The spring 79 is placed inside the inner cylinder 75. The balls 77 are resting against the cone shaped section 132 of the pins 120 inside the inner cylinder 75. The inner cylinder 75 is inside the arbor 70. There is at least one longitudinal groove 71 inside the arbor 70 extending into the area where the balls contact the arbor 70 through the recesses in the inner cylinder 75. When the spring-loaded ball locking mechanism is enabled, the balls 77 are pushed against a corresponding groove 71 and are locking the inner cylinder to the arbor 70. The balls 77 are pushed through a corresponding recess in the inner cylinder 75 as described above. When the spring-loaded ball lock mechanism is enabled, the inner cylinder and the arbor are rotatable locked to each other. Pushing the pins 120 in the longitudinal direction of the inner cylinder the balls 77 will disengage the balls from the groove and let the arbor rotate freely. The inner cylinder 75 is coupled directly or via gear wheels to the locking wheel, whereby undesired rotations of the inner cylinder are prevented. When pulling the pull-cord, the linear movement of the pull-cord is transformed into rotations of the reel. Rotation of the reel is then transmitted via a coupling comprising gear wheels 62, 64 to the inner cylinder 75 whereby rotating the arbor 70 and winding up the strap 40. As long as the spring load ball locking mechanism is enabled the inner cylinder 75 and arbor 70 rotate together. The locking wheel 90 is connected to the inner cylinder 75 and will prevent unwinding of the strap wound up on the arbor 70. When the spring-loaded ball locking mechanism is disengaged by pressing the pins 130, the arbor may rotate and unwind the strap. The inner cylinder is, due to its coupling to the locking wheel, prevented from rotating in the direction that unwinds the strap.

This simple and efficient release mechanism has the advantage that the tension of the tourniquet may be released and reapplied easily. The release mechanism relocks the rotations of the arbor when the push pins are released. It is common to rapidly apply and tighten a tourniquet around bleeding limbs as a first treatment step to save life. After the tourniquet has been applied, one will typically reassess within certain intervals whether a constriction is further needed by releasing or adjusting the tourniquet.

In other embodiments (not shown), there may be more than two balls in the release mechanism to accommodate more fine-grained control of the release mechanism.

In other embodiments (not shown), the release mechanism may comprise one push pin to simplify manufacturing or make the system easier to operate.

The release mechanism may in other embodiments be provided with other means suitable to achieve comparable effects such as releasable friction locks or other means that may let the arbor temporarily unwind the strap.

The arbor may be coupled to other means suitable to prevent undesired unwinding of the strap e.g. locking arms, brakes, one way rotational locks or similar. In some embodiments with release mechanisms there may be means to prevent undesired rotations of the arbor during tightening of the tourniquet like locking wheels, brakes, or one-way rotational locks.

In another embodiment (not shown), the tourniquet comprises a tandem formation with two arbors for simultaneous winding up the first and the second end of the strap arranged around a limb. In this embodiment, the tourniquet comprises a pull-cord reel as described for any of the preceding figures, a first and a second arbor and an appropriate gearing mechanism transferring the rotational movement obtained by activating the pull-cord to both arbors. A housing provides support for the mechanics. Thereby, the housing has two openings allowing the strap to be wound up simultaneously by two arbors. The first end of the strap may be secured to the first arbor and the second end of the strap may be secured to the second arbor. A gear mechanism is provided which is mechanically coupled to the pull-cord reel, the first arbor and the second arbor. A pull-cord is wound up on the pull-cord reel. The first end of the pull-cord is secured to the reel and the second end of the pull-cord is free to be pulled. Upon pulling the second end of the pull-cord the reel rotates. Rotations of the reel are translated to rotations of the two arbors. In use the first end of the strap is secured to the first arbor. The second end is wrapped around the wounded limb. Thereafter the second end is secured to the second arbor. The strap and the arbor may be provided with means for shortening to provide gross tension by cinching around the limb. Pulling the pull-cord will further provide tension around the limb by winding the strap on to the first and second arbor. The transmission of the rotation of the reel may be translated as equal rotations on both the arbors. Rotations of the reel may alternatively be translated at different ratios to the first and second arbor. This is advantageous in allowing different sizing of the arbors, in particular when available space differs inside the housing around each of the arbors.

In another embodiment (not shown), the tourniquet comprises a combined arbor and pull-cord reel. In this embodiment the combined arbor and pull-cord reel are connected via a coupling in the longitudinal axis of the arbor and pull-cord reel. A housing provides support for the mechanics. Thereby, the housing has an opening allowing the strap to be wound up by the arbor. The first end of the strap is secured to the arbor. The second end of the strap may be secured to the housing. A pull-cord is wound up on the pull-cord reel. The first end of a pull-cord is secured to the reel and the second end of the pull-cord is free to be pulled. Upon pulling the second end of the pull-cord the reel rotates. Rotations of the pull-cord reel are translated to rotations of the arbor via the direct coupling between the arbor and the pull-cord reel. In use the first end of the strap is secured to the arbor. The second end is wrapped around the wounded limb. Thereafter the second end is secured to the housing. The strap may be provided with means for shortening to provide gross tension by cinching of the limb. Pulling the pull-cord will further provide tension around the limb by winding the strap on to the arbor. The disadvantage of this simplified embodiment is that there is no translation by gear wheels between the rotating reel and the arbor which results in that the forces applied by pulling the pull-cord needed to constrict the tourniquet are much higher.

In some embodiments, the coupling comprises a clutch mechanism, as described in the preceding sections, allowing rewinding of the pull-cord on to the recoil reel. In some embodiments, the coupling is a direct connection where the arbor and the pull-cord reel share a common shaft. An advantage of a common shaft is to simplify manufacture of the tourniquet. In some embodiments, the coupling between the arbor and the pull-cord reel may be a combination of a clutch mechanism and/or gear wheels. This arrangement of a clutch mechanism and/or gear wheel may be advantageous to allow rewinding of the pull-cord and/or different translation rate of rotations of the pull-cord reel to the arbor.

In the preceding embodiments the reel should be understood to have a longitudinal axis that may rotate upon pulling the attached pull-cord. Similarly, the arbor should be understood to have a longitudinal axis that may rotate for winding up a strap. The coupling between the reel and the arbor may comprise elements from a list of gear systems, gear wheels, clutches, direct connections etc. An advantage of the coupling is to transfer rotations of the reel to rotations of the arbor. The reel and at least one arbor can be mounted parallel in the housing. In other embodiments, the reel and arbor may be mounted non-parallel in the housing to allow an optimized sizing of the tensioning device. In some embodiments, the reel and arbor may be mounted coaxially.

In at least some embodiments of the tourniquet, the rotation axis of the pull-cord reel is perpendicular to the rotation axis of the arbor. Pulling the pull-cord rotations from the reel is translated to rotations of the arbor that wind up the strap on the arbor. The translation of the rotations of the pull-cord reel to the arbor may be performed by gear wheels or similar solutions known to the skilled person in the field. In some embodiments, the possibility to pull the pull-cord upwards away from the tightening mechanism and injured limb is maintained such as by a suitable guiding mechanism, a wheel or similar. Such an arrangement where the pull-cord reel is perpendicular to the arbor accommodates the possibility for a larger pull-cord reel and a greater length of the pull-cord and a simpler design of the rewind mechanism of the pull-cord reel.

In some embodiments of the tourniquet, the arbor is provided with a mechanism that allows for adjusting the initial constriction (gross cinching) of the tourniquet before the tightening of the tourniquet by pulling the pull-cord by means of the first strap. The tensioning mechanism comprises the arbor for winding up the first end of the strap as described above. Instead of the first end of the strap being attached to the arbor, the free end of the first end of the strap can be passed through the arbor. The arbor may be a cylinder provided with a slot where the free end of the first end of the strap is passed through.

The arbor is in addition provided with a brake mechanism that prevents the strap from reverse movement through the arbor. In use of the tourniquet the strap is first wrapped around a limb and the second end of the strap is attached to the housing by using a quick lock mechanism. The free end of the first end is passed through the arbor and out of the housing. Pulling the free end of the first end of the strap will further tighten the strap around the limb. The subsequent tightening is performed by pulling the handle of the pull-cord reel. The pulling of the pull-cord reel converts the linear movement of the pull-cord to rotational movement of the arbor. The first end of the strap is then wound up on the arbor. The first end of the strap may be provided with a handle or the like that makes holding and pulling easy. The brake mechanism in the arbor may be made of three parallel cylinders forming a friction brake. The strap can be passed around the cylinders in a winding path which due to friction is preventing the strap from reverse movement through the arbor. When rotating the arbor, with these cylinders, the first end of the strap is wound up on the arbor and the strap is tightened around the limb for better occlusion. The pull-cord reel may be perpendicular to the rotation axis of the arbor to save space of the tensioning mechanism. The quick lock assembly may be a magnetic quick lock for securing the second end of the strap to the housing. In other embodiments of the tourniquet the arbor is a cylinder provided with a longitudinal opening where the free end of the first end of the strap is passed through. The opening in the arbor is provided with teeth or friction area preventing the strap from reverse movement. In some embodiments the tourniquet 10 is provided with padding between the base 32 and skin of the limb. The padding is provided to prevent damage to the limb and prevent pinching of the skin during tightening of the tourniquet. The padding may be made of rubber, foam, fabric or other material suitable to protect the limb from the hard surface of the base.

In some embodiments, the tourniquet 10 is provided with a strap 40 made of a smart textile. The smart textile may indicate a level of tension applied to a limb by the tourniquet. The smart textile may indicate tension or stretching in a certain direction by change of color, pattern, sounds or odor. This may be used to indicate to the operator that sufficient tightening of tourniquet is attained or that not sufficient tightening is not applied.

In case of an emergency where rapid occlusion of a bleeding limb is needed the described tourniquet 10 may be used. The tourniquet 10 may be wrapped in a container or bag such as a plastic bag that may easily be opened with one hand. The tourniquet 10 is unwrapped from the plastic bag. The tensioning device 20 with the first end 42 of the strap 40 attached is placed on the limb/extremity above the bleeding wound. The free end of the strap 40 is thereafter wrapped around the limb above the bleeding wound. The free end of the strap 40 is fixed through a lock cylinder 82 to the housing of the tensioning device 20 (e.g., on the base 32 of the housing). The tourniquet is tensioned by cinching the strap 40 using the lock cylinder 82 and the locking ring 84. The subsequent tightening of the tourniquet is performed by pulling the handle 52 of the pull-cord 54. The rewind functionality of the recoil reel 50 will allow several repetitions of the pulling the handle 52 of the pull-cord 54 and releasing the handle 52. The repetitions of the tightening procedure will be repeated until a sufficient tension is applied by the tourniquet to stop bleeding from the limb. The tourniquet 10 may be released by e.g. removing the release pin 120 by pulling the ring 122 as described for the second embodiment or by pushing the push pins 130 of the ball locking mechanism as described for the third embodiment.

The tourniquet may also be adapted to apply direct pressure on a flesh wound. For example, the tourniquet may be used with a gauze pad to apply direct pressure on the wound. The tension or amount of pressure applied by the tourniquet may be rapidly applied by the tensioning mechanism.

The tourniquet may be adapted for reuse. For example, the housing is adapted for being suitably sterilized and the strap may be replaced with a new sterile strap. It may also be possible to sterilize at least parts of the tourniquet to enable reuse of parts or the complete tourniquet.

In at least some embodiments, the materials for the tourniquet are materials that may be sterilized and/or that are aseptic.

Some tourniquet designs may cause excess slack in the strap that wraps around a limb. This excess slack may be present when the tourniquet is initially placed on a limb. Slack may be a significant technical problem and may cause delay, injury, or misuse when the tourniquet is used. For example, the tourniquet may slide/move from a desired location on a limb to a less desired location where the tourniquet may not be as effective. Slack in the tourniquet may also allow the strap of the tourniquet to twist, resulting in uneven or unintended pressure (or squeezing) and potential injury to the skin or limb. Furthermore, slack in the tourniquet may delay therapeutic application of the tourniquet as the tourniquet is tightened to fit the limb, resulting in additional blood loss as well as delay in critical field operations under time pressure. Additionally, excess slack may limit the effectiveness of some existing tourniquet designs as the windlass or other tightening mechanism may not be able to build up enough pressure after removing any existing slack.

Figure 9:
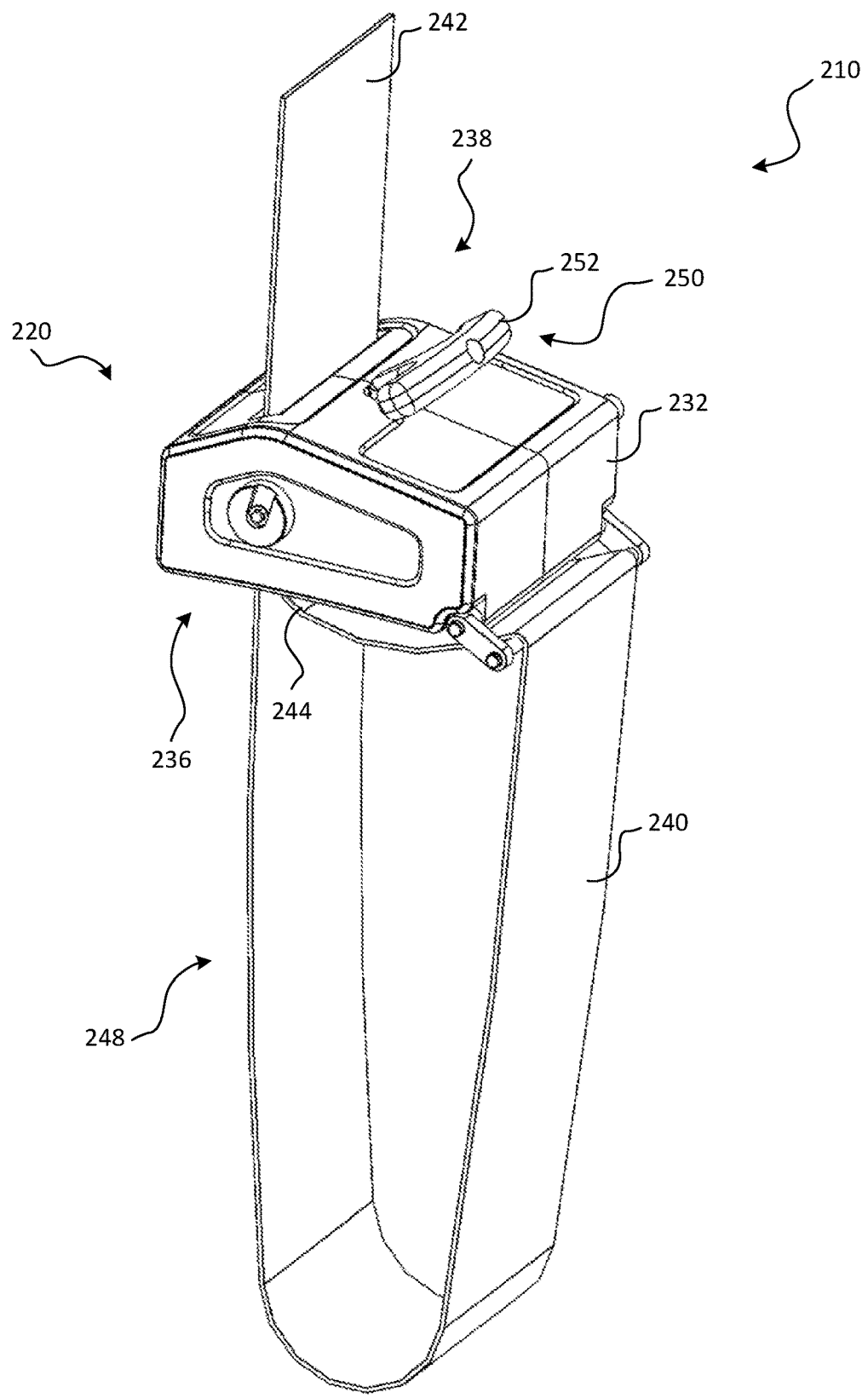
FIG. 9 is a schematic diagram of another embodiment of a tourniquet.

FIG. 9 is a schematic diagram of another embodiment of a tourniquet 210.

The tourniquet 210 may eliminate or reduce many of the problems caused by excess slack that are present in some other tourniquet designs.

The tourniquet 210 includes a strap 240 and a tensioning device 220. The strap 240 can be arranged in a loop 248 to go around a limb. The tensioning device 220 is coupled to the strap 240 and can be used to increase or decrease tension in the strap 240. For example, tension in the strap 240 may be increased by reducing the size of the loop 248. As the tension increases, the tourniquet 210 puts more pressure on the limb to reduce or stop blood flow through the limb.

The tensioning device 220 includes a housing 232 and a pull-cord assembly 250. The strap 240 includes a first end 242 and a second end 244. The strap 240 passes through the housing 232, allowing a user to pull the first end 242 of the strap 240 to advance the strap 240, tightening the tourniquet 210 and removing slack in the strap 240. The pull-cord assembly 250 can then be used to further tighten the tourniquet 210.

In some embodiments, the strap 240 passes through the housing 232, entering through a first slot 236 in the housing 232 and exiting through a second slot 238 in the housing 232. The first end 242 of the strap 240 may be free (e.g., unattached) and the second end 244 of the strap 240 may be attached to the housing 232.

The first slot 236 and the second slot 238 may be disposed on different sides of the housing 232. For example, the first slot 236 may be disposed on a proximal side of the housing 232 (i.e., a side closer to the limb when the tourniquet is used) and the second slot 238 may be disposed on a distal side of the housing 232 (i.e., a side further from the limb is used). In some embodiments, the first slot 236 and the second slot 238 are on opposite sides of the housing 232. The first slot 236 and the second slot 238 may be on adjacent sides of the housing 232 or on the same side of the housing 232.

The loop 248 is formed in a portion of the strap 240 that extends from the second end 244 to the first slot 236. When the tourniquet 210 is used, the loop 248 is placed (or formed) around a limb. The first end 242 can then be pulled to advance more of the strap 240 through the housing 232, causing the loop 248 to tighten around the limb. The tensioning device 220 may be configured to permit the strap 240 to advance further through the housing 232 (e.g., toward the first end 242, tightening the loop 248) but not to be pulled back out of the housing 232 (e.g., back towards the loop 248, expanding the loop 248).

The first end 242 may initially be pulled by hand to achieve an initial gross tensioning of the tourniquet 210. This gross tensioning of the tourniquet 210 may allow a user to quickly eliminate slack to achieve a snug fit and securely position the strap 240 and the tensioning device 220 at a desired location on the limb. The user can then further tighten the tourniquet 210 to a desired tension level by pulling a handle 252 of the pull-cord assembly 250, which may provide a mechanical advantage in further advancing the strap 240 through the housing 232.

Beneficially, because the strap 240 passes through the housing 232, the tourniquet 210 can be initially tightened (or grossly tensioned) initially with a hand pull so that the length of the loop 248 approximately matches the perimeter of the limb. This initial tightening eliminates most or all of the slack in the loop 248. This initial tensioning does not typically require any mechanical assistance as there will be little resistance to tightening the strap 240 until the loop 248 snugly fits the limb.

The pull-cord assembly 250 includes the pull-cord handle 252, a pull-cord reel 251 (not shown), and a pull-cord 254 (not shown). The pull-cord reel 251 may be similar to the previously described pull-cord reel 50 and the pull-cord 254 may be similar to the previously described pull-cord 54.

In some implementations, the second end 244 is removably attached to the housing 232 such that a user of the tourniquet may remove and re-attach the second end 244 to the housing 232. The second end 244 may be attached to the housing 232 with any type of fastening device, which may be similar to the previously described fastening means.

The housing 232 may have a concave bottom surface to better or more comfortably fit against a limb. In some embodiments, the housing 232 may include a pad on the bottom surface.

The housing 232 may include internal dividers that separate the interior of the housing into multiple regions. For example, the housing 232 may include a divider that separates the interior into a first region and a second region. The first region may include the arbors that interact with the strap 240. The first slot 236 and the second slot 238 may provide access to the first region. The second region may include some or all of the other components of the tensioning device 220 (e.g., the pull-cord reel 251 and components such as gear systems that provide a mechanical advantage). Beneficially, by separating the first region and the second region, the divider may prevent (or reduce) dust, dirt, and other grit that passes through the first slot 236 and the second slot 238 from accessing the second region where it may interfere with the function of the components therein. Furthermore, some embodiments may include brushes disposed along one or both of the first slot 236 and the second slot 238 or other components the limit or prevent dust, dirt, and grit from entering the first slot 236 or the second slot 238 (or from being pulled inside the housing with the strap 240).

Figure 10:
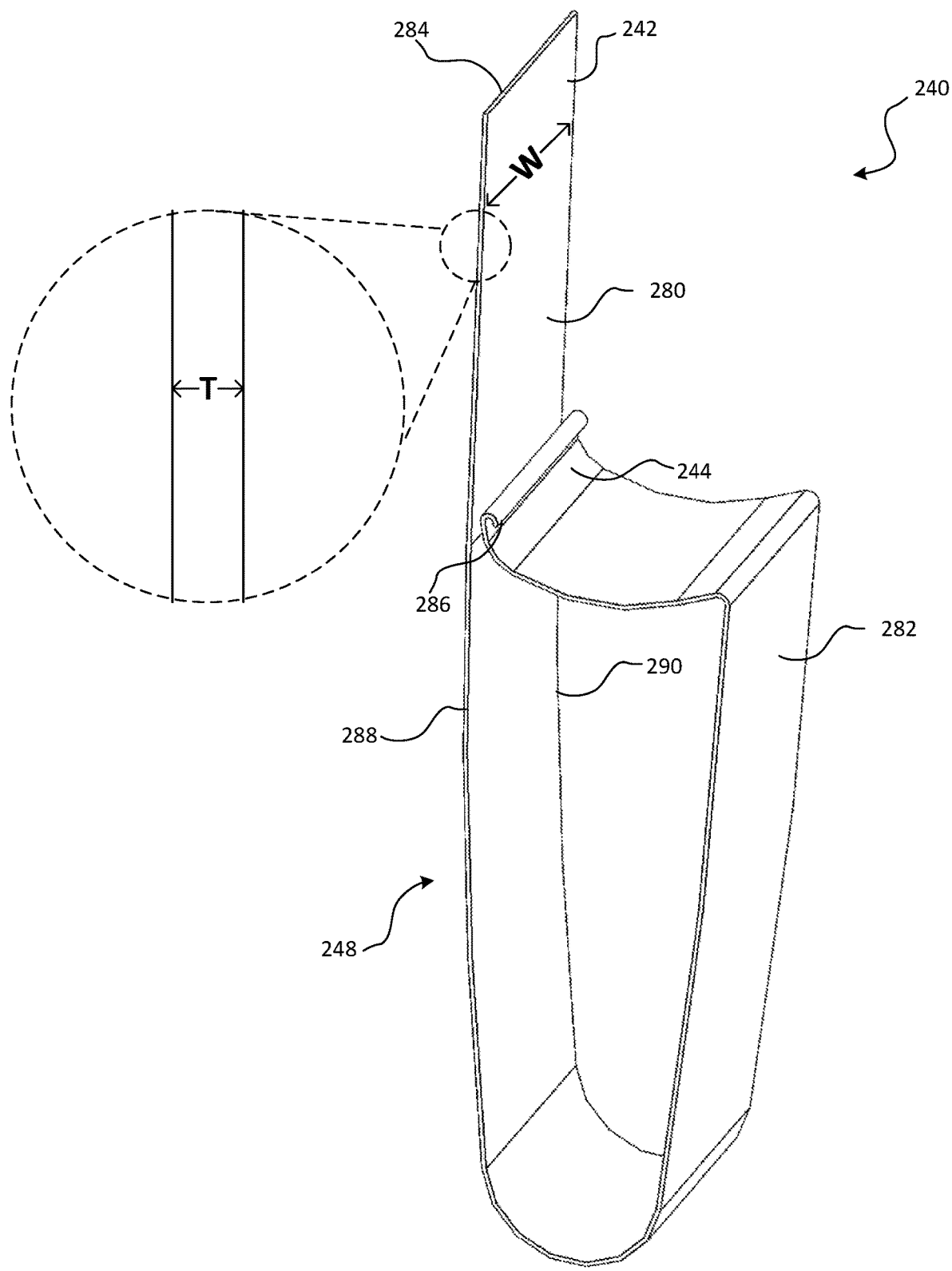
FIG. 10 is a schematic view of an example strap of the tourniquet of FIG. 9.

FIG. 10 is a schematic view of the strap 240 arranged to form the loop 248. The strap 240 has a first face (or surface) 280 and a second face (or surface) 282. The first face 280 and second face 282 extend the length and width of the strap. The first face 280 and second face 282 are separated from one another by the thickness of the strap 240.

In some embodiments, the strap 240 is formed from a compressible material such that if the material is squeezed, the material will compress, reducing the thickness of the strap 240. The material of the strap 240 may be squeezed when pressure is applied from opposite directions on the first face 280 and the second face 282. The material may be a resilient compressible material such that when the pressure is removed, the strap 240 returns to its original thickness.

The strap 240 also has a first short edge 284 and a second short edge 286. The first short edge 284 is on the first end 242 of the strap 240 and the second short edge 286 is on the second end 244 of the strap 240. The first short edge 284 and the second short edge 286 are separated from each other by the length of the strap 240.

The strap 240 also has a first long edge 288 and a second long edge 290. The first long edge 288 and the second long edge 290 are separated from each other by the width of the strap 240.

Although not shown, in some embodiments, the strap 240 is disposed within a sock (or holster strap). The sock may be configured to distribute pressure from the tourniquet more evenly across the width of the strap to, for example, reduce the strap digging into skin as the tourniquet is tightened.

Figure 11:
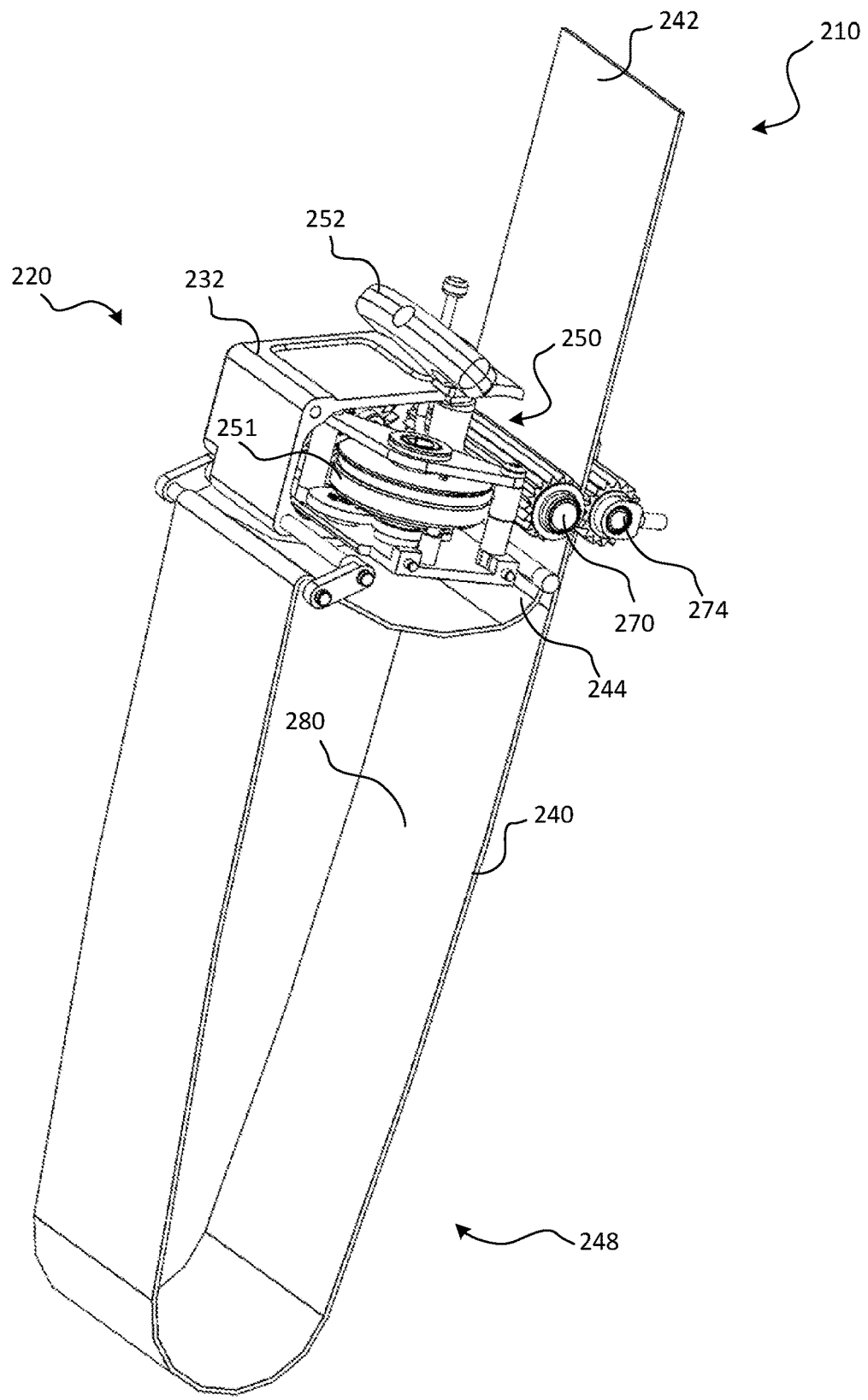
FIG. 11 is a schematic diagram of the tourniquet of FIG. 9 with a portion of the housing removed so that components of the tensioning device enclosed within the housing can be seen.
Figure 12:
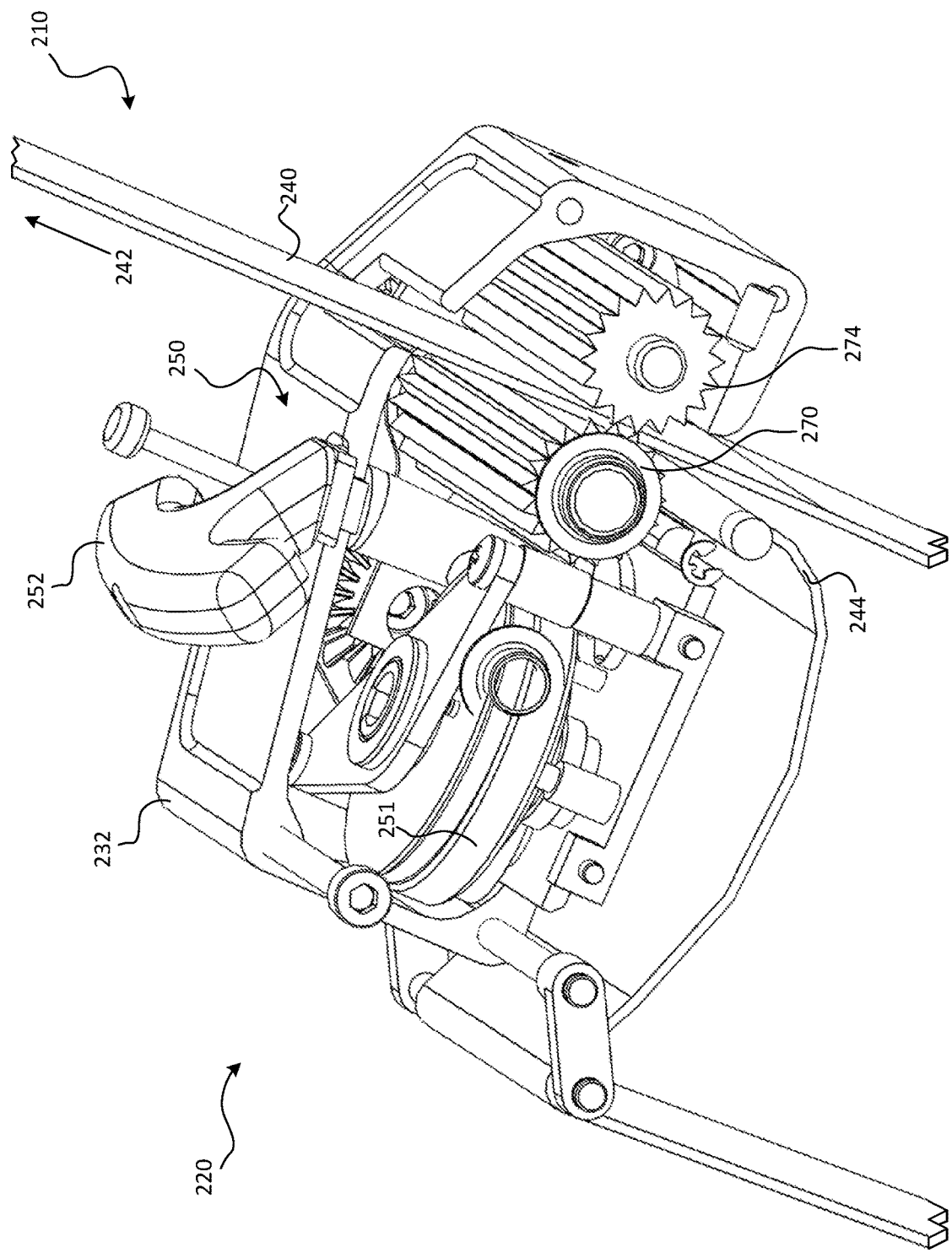
FIG. 12 is a schematic diagram of a close-up view of the components of the tensioning device enclosed within the housing of the tourniquet of FIG. 9.
Figure 13:
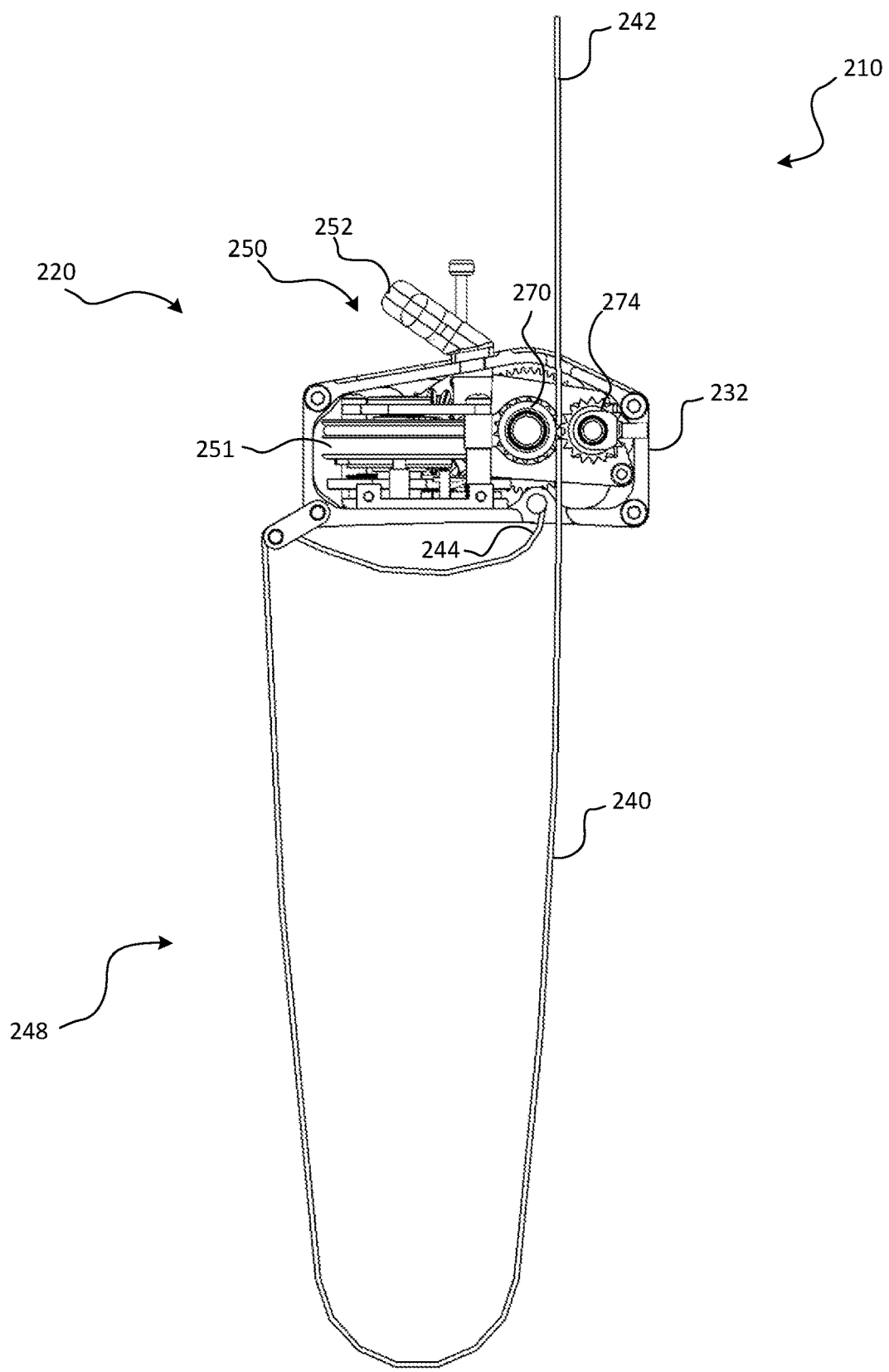
FIG. 13 is a schematic diagram of a cross-sectional view of the tourniquet of FIG. 9.

FIGS. 11-13 are schematic diagrams of the tourniquet 210. In FIG. 11, a portion of the housing 232 has been removed so that components of the tensioning device 220 enclosed within the housing 232 can be seen. In FIG. 12, a close-up view of the components of the tensioning device 220 enclosed within the housing 232 are shown. In FIG. 13, a cross-sectional view of the tourniquet 210 is shown.

As shown in this figure, the tensioning device 220 includes a driving arbor (or driving cylinder) 270 and a secondary arbor (or secondary cylinder) 274, both of which are disposed within the housing 232. The strap 240 is disposed between the driving arbor 270 and the secondary arbor 274. The driving arbor 270 may be coupled to the pull-cord reel 251 so that rotations of the pull-cord reel 251 cause the driving arbor 270 to rotate. For example, the pull-cord reel 251 may be coupled to the driving arbor 270 in a manner similar to those previously described with respect to the pull-cord reel 50 and the arbor 70.

In some implementations, the driving arbor 270 and the secondary arbor 274 are separated by a gap to allow passage of the strap 240. The first face 280 of the strap 240 may contact the driving arbor 270 and the second face 282 of the strap 240 may contact the secondary arbor 274. The gap may be sized to pinch (or squeeze) the strap so that the strap 240 cannot slide between the driving arbor 270 and the secondary arbor 274. Instead, the strap 240 may only move through the driving arbor 270 and the secondary arbor 274 when the driving arbor 270 and the secondary arbor 274 rotate. The tensioning device 220 may include a lock assembly that prevents one or both of the driving arbor 270 and the secondary arbor 274 from rotating in a direction that allows the strap 240 to move backward (i.e., toward the loop 248 to reduce tension). In at least some embodiments, the lock does not interfere with the rotation of the driving arbor 270 and the secondary arbor 274 in a direction that advances the strap 240 through the housing 232 (i.e., toward the first end 242 to increase tension in the loop 248).

Figure 14:
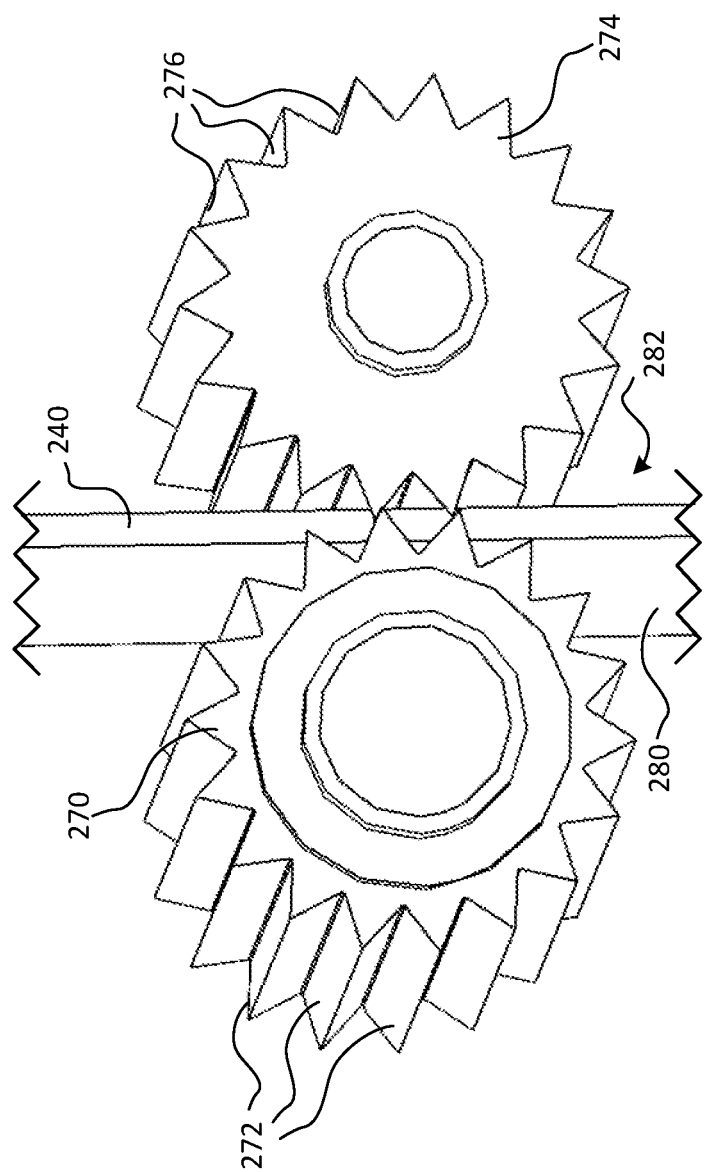
FIG. 14 is a schematic diagram of a close-up of the driving arbor and the secondary arbor of the tourniquet of FIG. 9.

FIG. 14 is a schematic diagram of a close-up of the driving arbor 270 and the secondary arbor 274. Also shown is the strap 240 passing between the driving arbor 270 and the secondary arbor 274.

Although alternatives are possible, the driving arbor 270 may include protrusions 272 and the secondary arbor 274 may include protrusions 276. The protrusions may, for example, be spaced equally around the exteriors of the driving arbor 270 and the secondary arbor 274. For example, the driving arbor 270 may include 18 equally spaced protrusions 272 and the secondary arbor 274 may include 18 equally spaced protrusions 276. The protrusions 272 and protrusions 276 may interlock (mesh) with one another to grip the strap 240 (e.g., to hold the strap 240 in place preventing loosening or to advance the strap through the housing 232 tightening the strap 240).

The protrusions 272 and protrusions 276 may have various shapes or sizes.

For example, the protrusions 272 and protrusions 276 may have pointed tips (e.g., where two planar surfaces meet in a corner) or rounded tips. The protrusions 272 and protrusions 276 may interlock without physically contacting one another. Instead, they may interlock while maintaining a gap distance between one another. For example, the protrusions 272 may align with gaps between the protrusions 276.

In some embodiments, the gap distance is equal to or approximately equal to the thickness of the strap 240. In some embodiments, the gap distance may be equal to or approximately equal to between 80% to less than 100% of the thickness of the strap 240 so as to squeeze the strap 240. In some embodiments, the gap may be slightly larger than the thickness of the strap 240.

In some embodiments, the protrusions 272 and the protrusions 276 may include teeth that bite into the strap 240 (e.g., penetrate into a surface of the strap 240). These teeth may hold the strap 240 in place relative to the driving arbor 270 and the secondary arbor 274 so that the strap 240 only moves through the housing 232 when the driving arbor 270 and the secondary arbor 274 rotate. For example, as the driving arbor 270 rotates, a portion of the teeth may penetrate the strap 240 and then pull the strap 240 in the direction of rotation until the teeth are pulled back out of the strap 240. As the rotation continues, a different portion of the teeth will penetrate the strap 240 and will continue to pull the strap 240 forward.

In some embodiments, some or all of the driving arbor 270 may be formed from a rigid material. In some embodiments, at least a portion of the driving arbor 270 is formed from a flexible material. For example, the driving arbor 270 may include an exterior coating formed from a flexible material such as rubber. Although the surface of the driving arbor 270 is shown as being smooth, alternatives are possible. Some embodiments of the driving arbor 270 may include one or more textured surfaces. For example, the textured surfaces may increase friction between the driving arbor 270 and the strap 240. Similarly, embodiments of the secondary arbor 274 are possible that include any of the surfaces properties or material types that have been described with respect to the driving arbor 270.

Although the exteriors of the driving arbor 270 and secondary arbor 274 are the same in FIG. 14, embodiments are possible in which the exteriors of the driving arbor 270 and the secondary arbor 274 are different too.

Figure 15:
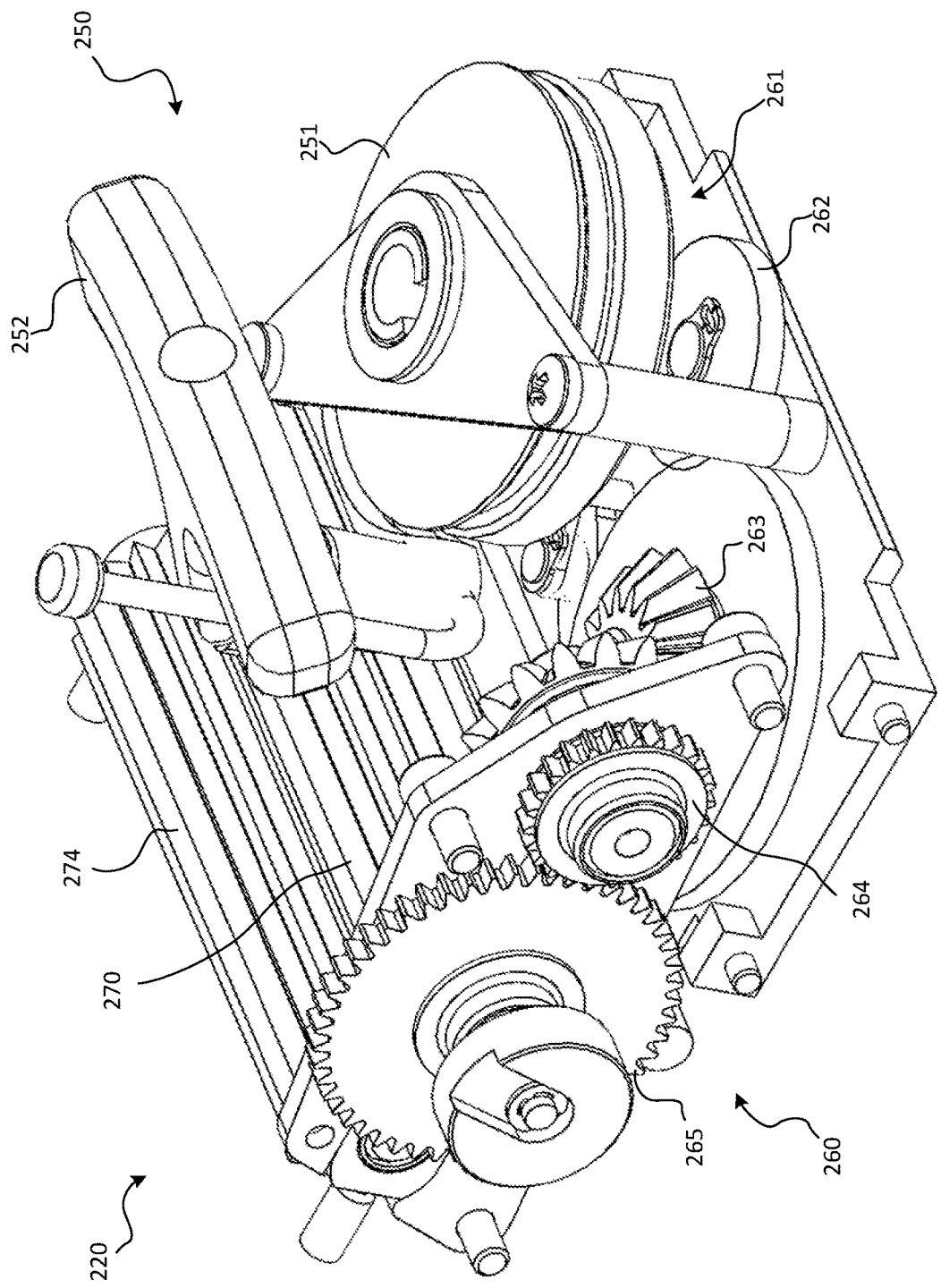
FIG. 15 is a schematic diagram of components of an example tensioning device of the tourniquet of FIG. 9.
Figure 16:
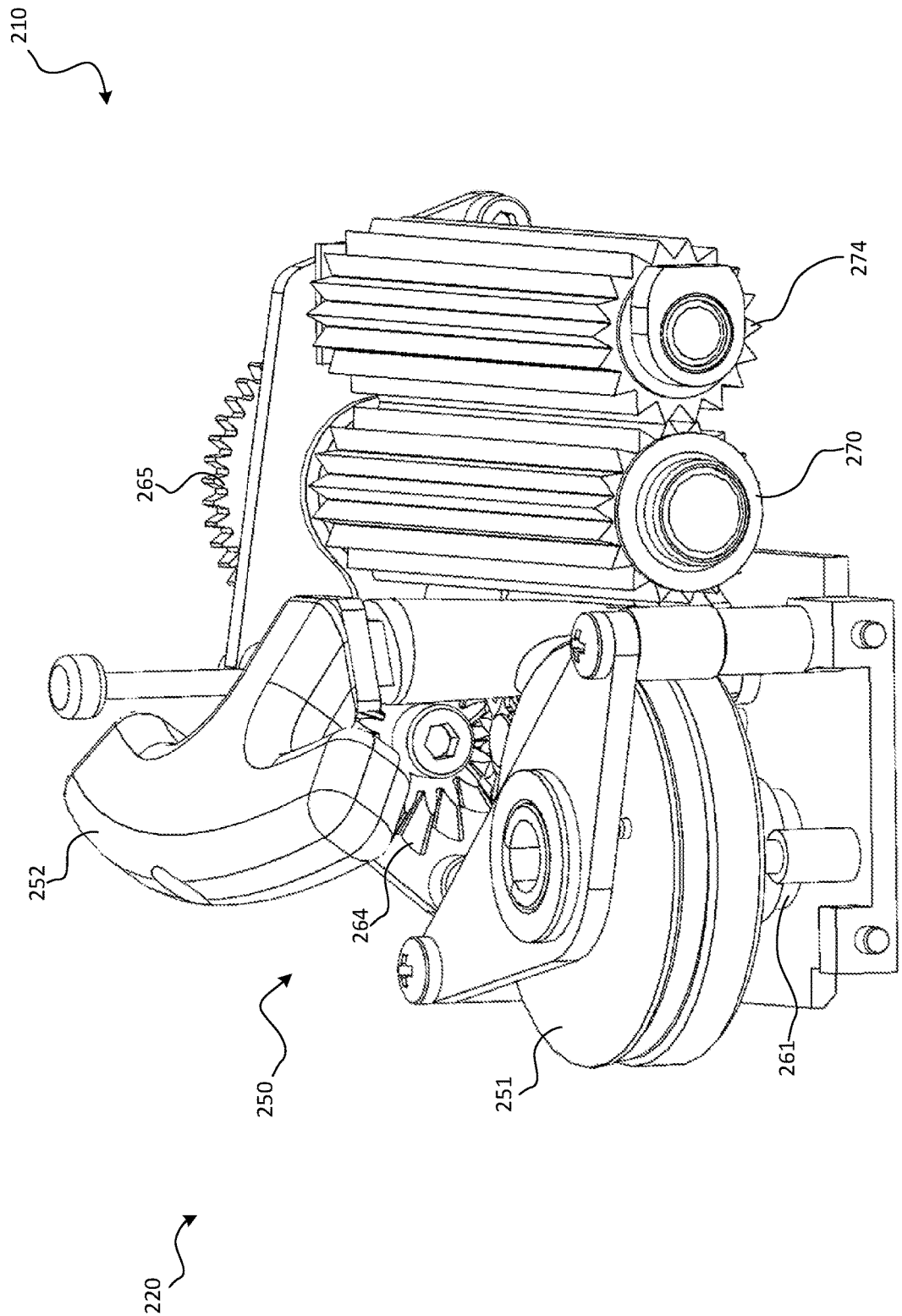
FIG. 16 is a schematic diagram of components of an example tensioning device of the tourniquet of FIG. 9.
Figure 17:
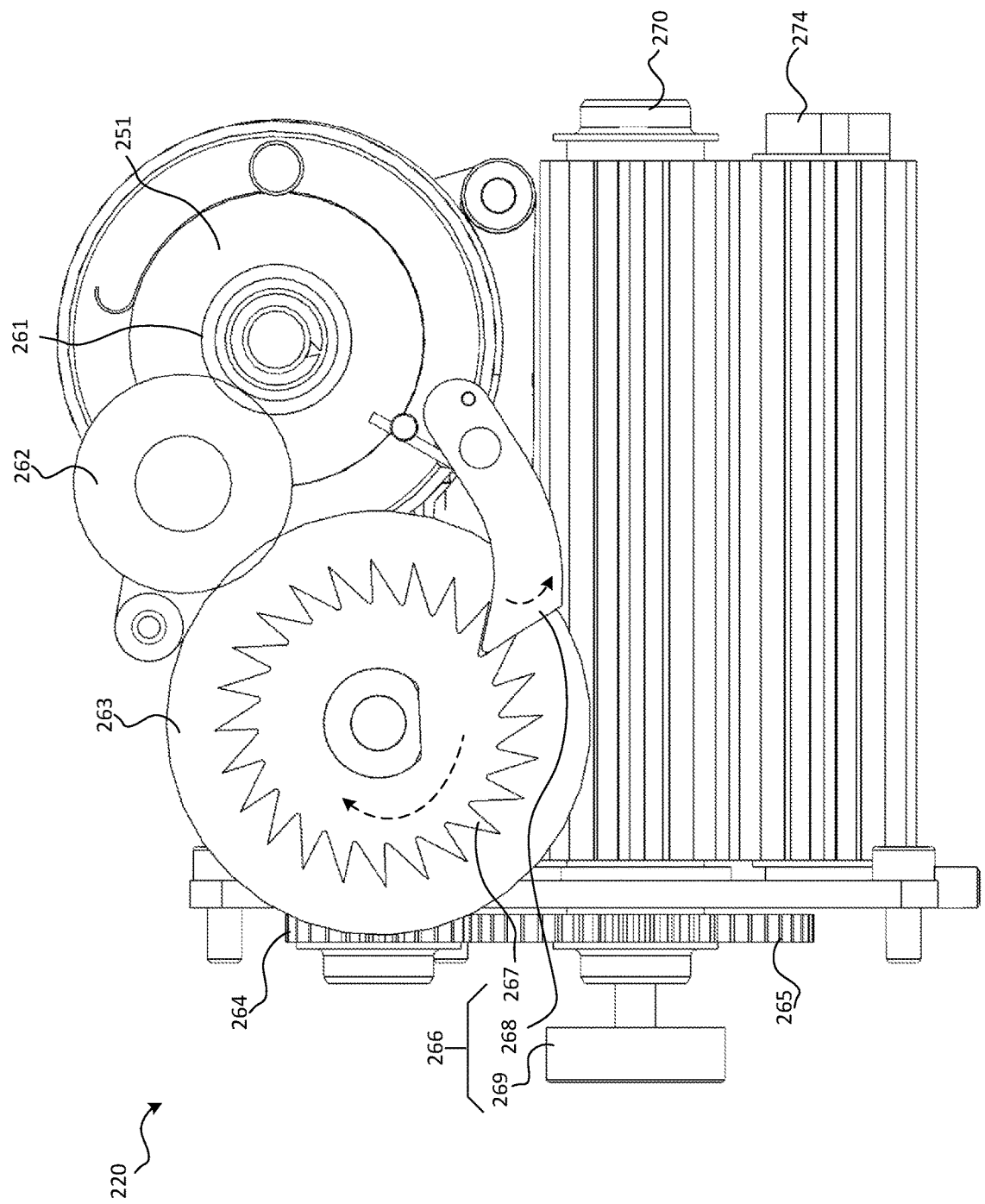
FIG. 17 is a schematic diagram of components of an example tensioning device of the tourniquet of FIG. 9.

FIGS. 15-17 are schematic diagrams of components of the tensioning device 220 of the tourniquet 210. In particular, a coupling assembly 260 is shown that couples the pull-cord assembly 250 to the driving arbor 270. FIG. 15 is an angled view of these components of tensioning device 220. FIG. 16 is a side view of these components of the tensioning device 220. FIG. 17 is a bottom view of these components of the tensioning device 220. It should be understood that FIGS. 15-17 do not show all of the components of the tensioning device 220 and some embodiments will include additional or different components. The coupling assembly 260 is an example of the previously described coupling.

In this example, the coupling assembly 260 is a mechanical advantage coupling assembly that provides a mechanical advantage in increasing the tension of the tourniquet 210 (i.e., tightening the tourniquet). Here, the coupling assembly 260 includes a gear arrangement that provides a mechanical advantage in translating linear motion applied by pulling the handle 252 of the pull-cord assembly to rotational motion of the driving arbor 270. Beneficially, this mechanical advantage may allow tightening the tourniquet 210 using less force than would be required without the mechanical advantage coupling assembly.

Here, the coupling assembly 260 includes a first gear 261, a second gear 262, a third gear 263, a fourth gear 264, and a fifth gear 265 (referred to collectively as gears). These gears may include teeth that interlock with each other so that rotations in one of the gears cause rotations in one or more of the other gears. As an example, the gears may interlock with each other by having teeth (not shown on all gears) that mesh with each other.

In this example, the first gear 261 interlocks with the second gear 262, the second gear 262 also interlocks with the third gear 263, the third gear 263 also interlocks with the fourth gear 264, and the fourth gear 264 also interlocks with the fifth gear 265. Through this chain of gears, rotations of the first gear 261 cause rotations of the fifth gear 265 via the second gear 262, third gear 263, and fourth gear 264.

Here, the first gear 261 is joined to the pull-cord assembly 250 such that rotations of the pull-cord reel 251 cause the first gear 261 to rotate. In this example, the first gear 261 shares an axel with the pull-cord reel 251. The fifth gear 265 is joined to driving arbor 270 such that rotations of the fifth gear 265 cause the driving arbor 270 to rotate.

Various embodiments may include various types of gears. For example, the third gear 263 and the fourth gear 264 are bevel gears and are oriented perpendicularly to each other. This arrangement of the third gear 263 and the fourth gear 264 allows the axis of rotation of the driving arbor 270 to be oriented perpendicularly with respect to the pull-cord reel 251.

Various embodiments may include various gear ratios between adjacent gears. Based on, for example, the number of teeth and the size of the gears, various gear ratios can be achieved between the interlocking gears (i.e., the ratio of the number of rotations in one gear to the number of turns in another gear). These gear ratios may provide a mechanical advantage in tightening the tourniquet. For example, the fifth gear 265 may have three times as many teeth as the fourth gear 264. Accordingly, the fourth gear 264 will complete three rotations to drive the fifth gear 265 through one rotation.

The coupling assembly 260 may include a lock 266 (FIG. 17). The lock 266 may prevent rotation of the driving arbor 270 in at least one direction. In at least some embodiments, the lock 266 includes a ratchet gear 267, a pawl 268, and a release 269.

The ratchet gear 267 includes angled teeth that are offset in one direction (i.e., the teeth are not symmetric across any radius extending from the center of the ratchet gear 267). The pawl 268 is a rigid elongate structure that is configured to rotate on a pin. The pawl 268 may be configured to rotate away from the ratchet gear 267 when pushed by the ratchet gear 267 (i.e., the pawl 268 may rotate in a counterclockwise direction in FIG. 17). In this manner, the pawl 268 does not interfere with rotation of the ratchet gear 267 in one direction (the clockwise direction in FIG. 17). The pawl 268 may be spring loaded so as to rotate back to its base position as shown in FIG. 17 when there is no pressure from the ratchet gear 267. The pawl 268, however, prevents rotation of the ratchet gear 267 in the other direction (i.e., the counterclockwise direction in FIG. 17).

The release 269 may disengage the pawl 268 from the ratchet gear 267 to allow free rotation of the ratchet gear 267 in either direction. The release 269 may, for example, include a button that when pushed causes the pawl 268 to rotate away from the ratchet gear 267.

Although the lock 266 has been illustrated and described as a component of the coupling assembly 260, alternatives are possible. Various other mechanisms of locking an arbor to prevent unintended rotation of an arbor have been previously described and may be included in embodiments to prevent rotation of the driving arbor 270.

Some non-limiting examples are provided below.

Example 1: A tourniquet comprising: a tensioning device that includes a housing and a pull-cord assembly; and a strap that passes through the housing, the strap having a first end and a second end, the strap being arranged to together with the housing form a loop for encircling a limb; wherein the pull-cord assembly is configured to advance the strap through the housing to tighten the loop.

Example 2: The tourniquet of example 1, wherein the second end of the strap is attached to the housing.

Example 3: The tourniquet of example 2, wherein the second end of the strap is removably attached to the housing.

Example 4: The tourniquet of any of examples 1-3, further comprising a driving arbor enclosed at least partially within the housing and a secondary arbor enclosed at least partially within the housing, wherein the strap passes between the driving arbor and the secondary arbor as the strap passes through the housing.

Example 5: The tourniquet of example 4, wherein the driving arbor and the secondary arbor are separated by a gap through which the strap passes.

Example 6: The tourniquet of example 5, wherein the strap is formed from a compressible material and the gap has a width that is less than an uncompressed thickness of the strap.

Example 7: The tourniquet of any of examples 4-6, wherein the pull-cord assembly is configured to advance the strap through the housing by causing the driving arbor to rotate.

Example 8: The tourniquet of example 7, wherein the driving arbor includes protrusions disposed along an exterior of the driving arbor.

Example 9: The tourniquet of example 8, wherein the secondary arbor includes protrusions disposed along an exterior of the secondary arbor.

Example 10: The tourniquet of example 9, wherein the protrusions of the driving arbor interlock with the protrusions of the secondary arbor to grip the strap.

Example 11: The tourniquet of any of examples 8-10, wherein the protrusions have pointed tips.

Example 12: The tourniquet of any of examples 8-11, wherein the protrusions include teeth that are shaped to penetrate at least partially into the strap.

Example 13: The tourniquet of any of examples 4-12, further comprising a coupling assembly that couples the pull-cord assembly to the driving arbor.

Example 14: The tourniquet of example 13, wherein the coupling assembly is a mechanical advantage coupling assembly.

Example 15: The tourniquet of example 14, wherein the mechanical advantage coupling assembly includes gears.

Example 16: The tourniquet of example 15, wherein the gears have a gear ratio greater than 1:1.

Example 17: The tourniquet of example 15, wherein the gears have a gear ratio greater than 2:1.

Example 18: The tourniquet of any of examples 13-17, wherein the coupling assembly is configured to decouple the pull-cord assembly from the driving arbor based on a level of tension applied to the limb exceeding a threshold level.

Example 19: The tourniquet of any of examples 4-18, wherein the tensioning device is configured to prevent further rotation of the driving arbor based on a level of tension applied to the limb exceeding a threshold level.

Example 20: The tourniquet of any of examples 4-19, wherein rotation of the driving arbor is controlled by a spring-loaded ball lock mechanism.

Example 21: The tourniquet of example 20, wherein the spring-loaded ball lock mechanism prevents rotation of the driving arbor based on a level of tension applied to the limb exceeding a threshold level.

Example 22: The tourniquet of any of examples 4-21, further comprising a lock that prevents loosening of the strap, wherein the lock prevents loosening of the strap by preventing rotation of the driving arbor in a first direction and allows rotation of the driving arbor in a second direction, the first direction being opposite of the second direction.

Example 23: The tourniquet of example 22, wherein the lock includes a ratchet gear and a pawl.

Example 24: The tourniquet of any of examples 22-23, wherein the lock includes a release that allows loosening of the strap.

Example 25: The tourniquet of example 24, wherein the release includes a button that when pressed allows rotation of the driving arbor in the first direction.

Example 26: The tourniquet of any of examples 4-25, wherein a rotation axis of the driving arbor is perpendicular to a rotation axis of a pull-cord reel of the pull-cord assembly.

Example 27: The tourniquet of any of examples 1-26, wherein the pull-cord assembly includes a pull-cord and a pull-cord reel that includes a recoil device for recoiling the pull-cord on the pull-cord reel.

Example 28: The tourniquet of any of examples 1-27, wherein the strap is made of a smart textile for indicating tension applied to the limb.

Example 29: The tourniquet of any of examples 1-28, further comprising a release mechanism for preventing the tourniquet being tensioned over a threshold tensioning degree.

Example 30: The tourniquet of any of examples 1-29, further comprising a lock that prevents loosening of the strap.

Example 31: The tourniquet of any of examples 1-30 for use in a medical treatment.

Example 32: The tourniquet of any of examples 1-31 for use to control and stop venous and arterial blood circulation to an extremity for a period of time.

Example 33: The tourniquet of any of examples 1, wherein the loop formed with the strap is arranged around a limb/extremity and thereafter tightened by pulling on the first end to remove slack, and then further tightened by pulling the pull-cord to advance the strap through the housing.

Example 34: The tourniquet of any of examples 1-33, wherein the strap is at least partially enclosed in a sock.

Example 35: The tourniquet of example 34, wherein the sock is configured to distribute pressure from the strap on the limb.

Example 36: The tourniquet of any of examples 1-35, wherein the first end of the strap and the loop are on opposite sides of the housing.

Example 37: The tourniquet of any of examples 1-36, wherein the housing includes a first slot and a second slot and the strap passes through the first slot and the second slot.

Example 38: The tourniquet of example 37, wherein the loop is formed in a portion of the strap that extends from the second end of the strap to the first slot.

Example 39: The tourniquet of example 38, wherein the first slot and the second slot are disposed on opposite sides of the housing.

Example 40: The tourniquet of example 38, wherein the first slot and the second slot are disposed on adjacent sides of the housing.

Example 41: The tourniquet of example 38, wherein the first slot and the second slot are disposed on a same side of the housing.

Example 42: A tourniquet comprising: a strap having a first end and a second end; and a tensioning device including: a housing; a driving arbor for advancing the strap through the housing to increase tension in a loop formed with the strap; an attach mechanism configured to affix the second end of the strap to the housing; a pull-cord and a pull-cord reel, the pull-cord being configured to provide rotations to the pull-cord reel; a coupling assembly for transferring rotations from the pull-cord reel to the driving arbor, and a locking mechanism to prevent release of the strap.

Example 43: The tourniquet of example 42, wherein the coupling assembly includes a gear system.

Example 44: A tourniquet comprising: a strap having a first end and a second end; and a tensioning device including: a driving arbor; a pull-cord reel and a pull-cord for providing rotations to the pull-cord reel; and a gear system for translation of rotations from the pull-cord reel to the driving arbor, wherein the rotations of the driving arbor cause a loop formed in the strap to increase in tension.

Example 45: The tourniquet of example 44, wherein the gear system is configured such that one rotation of the pull-cord reel results in less than one rotation of the driving arbor.

Example 46: The tourniquet of any of examples 44-45, wherein a rotational axis of the pull-cord reel is perpendicular to a rotational axis of the driving arbor.

Example 47: A method of using a tourniquet comprising: encircling a limb/extremity with a loop formed with a strap of the tourniquet, wherein the strap passes through a housing of the tourniquet; pulling a first end of the strap to remove slack in the loop; and further tightening the loop by pulling a pull-cord of the tourniquet.

Example 48: The method of example 47, wherein the first end of the strap is disposed on an opposite side of the housing from the loop.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A tourniquet (210) comprising:
   a tensioning device (220) that includes a housing (232) and a pull-cord assembly (250);
   a strap (240) that passes through the housing, the strap having a first end (242) and a second end (244), the strap being arranged to form a loop (248) together with the housing for encircling a limb;
   wherein the pull-cord assembly (250) is configured to advance the strap (240) through the housing (232) to tighten the loop (248).

2. The tourniquet (210) of claim 1, further comprising a driving arbor (270) enclosed at least partially within the housing (232) and a secondary arbor (274) enclosed at least partially within the housing, wherein the strap (240) passes between the driving arbor and the secondary arbor as the strap passes through the housing, wherein the driving arbor (270) and the secondary arbor (274) are separated by a gap through which the strap (240) passes and the strap (240) is formed from a compressible material and the gap has a width that is less than an uncompressed thickness of the strap.

3. The tourniquet (210) of claim 2, further comprising a coupling assembly (260) that couples the pull-cord assembly (250) to the driving arbor (270).

4. The tourniquet (210) of claim 3, wherein the coupling assembly (260) is a mechanical advantage coupling assembly.

5. The tourniquet (210) of claim 4, wherein the mechanical advantage coupling assembly includes gears.

6. The tourniquet (210) of claim 2, further comprising a lock (266) that prevents loosening of the strap (240), wherein the lock prevents loosening of the strap (240) by preventing rotation of the driving arbor (270) in a first direction and allows rotation of the driving arbor in a second direction, the first direction being opposite of the second direction.

7. The tourniquet (210) of claim 1, further comprising a driving arbor (270) enclosed at least partially within the housing (232) and a secondary arbor (274) enclosed at least partially within the housing, wherein the strap (240) passes between the driving arbor and the secondary arbor as the strap passes through the housing, wherein the pull-cord assembly is configured to advance the strap (240) through the housing (232) by causing the driving arbor (270) to rotate and the driving arbor (270) includes protrusions (272) disposed along an exterior of the driving arbor.

8. The tourniquet (210) of claim 7, wherein the secondary arbor (274) includes protrusions (276) disposed along an exterior of the secondary arbor.

9. The tourniquet (210) of claim 8, wherein the protrusions (272) of the driving arbor (270) interlock with the protrusions (276) of the secondary arbor (274) to grip the strap (240).

10. The tourniquet (210) of claim 7, wherein the protrusions (272, 276) have pointed tips.

11. The tourniquet (210) of claim 7, wherein the protrusions (272, 276) include teeth that are shaped to penetrate at least partially into the strap (240).

12. The tourniquet (210) of claim 1, wherein the pull-cord assembly (250) includes a pull-cord (254) and a pull-cord reel (251) that includes a recoil device for recoiling the pull-cord on the pull-cord reel.

13. The tourniquet (210) of claim 1, wherein the strap (240) is at least partially enclosed in a sock.

14. The tourniquet (210) of claim 13, wherein the sock is configured to distribute pressure from the strap (240) on the limb.

15. A tourniquet (210) comprising:
a tensioning device (220) that includes a housing (232) and a pull-cord assembly (250);
a strap (240) that passes through the housing, the strap having a first end (242) and a second end (244), the strap being arranged to together with the housing form a loop (248) for encircling a limb;
wherein the pull-cord assembly (250) is configured to advance the strap (240) through the housing (232) to tighten the loop (248), and
wherein the first end of the strap (240) and the loop are on opposite sides of the housing (232).

16. The tourniquet (210) of claim 15, wherein the housing (232) includes a first slot (236) and a second slot (238) and the strap (240) passes through the first slot and the second slot.

17. The tourniquet (210) of claim 16, wherein the loop (248) is formed in a portion of the strap (240) that extends from the second end (244) of the strap to the first slot (236).

18. A tourniquet (210) comprising:
a strap (240) having a first end (242) and a second end (244); and
a tensioning device (220) including:
a driving arbor (270);
a pull-cord reel (251) and a pull-cord (254) for providing rotations to the pull-cord reel; and
a gear system for translation of rotations from the pull-cord reel (251) to the driving arbor (270), wherein the rotations of the driving arbor cause a loop formed in the strap (240) to increase in tension.

19. The tourniquet (210) of claim 18, wherein the gear system is configured such that one rotation of the pull-cord reel (251) results in less than one rotation of the driving arbor (270).

20. The tourniquet (210) of claim 18, wherein a rotational axis of the pull-cord reel (251) is perpendicular to a rotational axis of the driving arbor (270).

* * * * *